United States Patent
Quaid, III

(12) 
(10) Patent No.: US 11,076,918 B2
(45) Date of Patent: *Aug. 3, 2021

(54) ROBOTICALLY-ASSISTED CONSTRAINT MECHANISM

(71) Applicant: MAKO Surgical Corp., Fort Lauderdale, FL (US)

(72) Inventor: Arthur E. Quaid, III, North Miami, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/785,939

(22) Filed: Feb. 10, 2020

(65) Prior Publication Data

US 2020/0170716 A1 Jun. 4, 2020

Related U.S. Application Data

(63) Continuation of application No. 15/431,542, filed on Feb. 13, 2017, now Pat. No. 10,610,301, which is a (Continued)

(51) Int. Cl.
*A61B 5/00* (2006.01)
*A61B 34/10* (2016.01)
(Continued)

(52) U.S. Cl.
CPC .......... *A61B 34/10* (2016.02); *A61B 17/1703* (2013.01); *A61B 17/3403* (2013.01);
(Continued)

(58) Field of Classification Search
CPC .... A61B 2017/00119; A61B 2034/107; A61B 34/20; A61B 34/30; A61B 2034/2055;
(Continued)

(56) References Cited

U.S. PATENT DOCUMENTS

| 4,747,393 A | 5/1988 | Medwid |
| 4,903,536 A | 2/1990 | Salisbury et al. |

(Continued)

FOREIGN PATENT DOCUMENTS

| AU | 2007254159 | 7/2013 |
| EP | 1 059 067 A1 | 12/2000 |

(Continued)

OTHER PUBLICATIONS

Martelli et al., "Computerand Robot Assisted Total Knee Replacement: Analysis of a New Surgical Procedure", Annals of Biomedical Engineering, vol. 28, pp. 1146-1153 (Year: 2000).*

(Continued)

*Primary Examiner* — Christopher L Cook

(74) *Attorney, Agent, or Firm* — Foley & Lardner LLP

(57) ABSTRACT

A surgical system includes a robotic arm, a constraint mechanism coupled to the robotic arm, and a computer system configured to control the robotic arm to constrain manual movement of the constraint mechanism to a plane. The computer system is also configured to control the robotic arm to lock the constraint mechanism in a desired pose when the constraint mechanism is moved to the desired pose via manual movement in the plane.

20 Claims, 12 Drawing Sheets

Related U.S. Application Data continuation of application No. 13/347,330, filed on Jan. 10, 2012, now abandoned, which is a continuation of application No. 10/384,078, filed on Mar. 6, 2003, now Pat. No. 8,095,200.

(60) Provisional application No. 60/362,368, filed on Mar. 6, 2002.

(51) Int. Cl.

| | | |
|---|---|---|
| *A61B 17/34* | (2006.01) | |
| *A61B 90/00* | (2016.01) | |
| *A61B 34/20* | (2016.01) | |
| *A61B 34/35* | (2016.01) | |
| *A61B 34/00* | (2016.01) | |
| *A61B 34/30* | (2016.01) | |
| *A61B 34/32* | (2016.01) | |
| *A61B 34/37* | (2016.01) | |
| *A61B 17/17* | (2006.01) | |
| *B25J 9/00* | (2006.01) | |
| *B25J 13/02* | (2006.01) | |
| *A61B 17/00* | (2006.01) | |

(52) U.S. Cl.
CPC ............ *A61B 34/20* (2016.02); *A61B 34/25* (2016.02); *A61B 34/30* (2016.02); *A61B 34/32* (2016.02); *A61B 34/35* (2016.02); *A61B 34/37* (2016.02); *A61B 34/70* (2016.02); *A61B 34/74* (2016.02); *A61B 34/76* (2016.02); *A61B 34/77* (2016.02); *A61B 90/03* (2016.02); *A61B 90/06* (2016.02); *A61B 90/36* (2016.02); *A61B 90/39* (2016.02); *B25J 9/0081* (2013.01); *B25J 13/025* (2013.01); *A61B 17/1757* (2013.01); *A61B 17/1767* (2013.01); *A61B 2017/00022* (2013.01); *A61B 2017/00119* (2013.01); *A61B 2017/00128* (2013.01); *A61B 2017/00199* (2013.01); *A61B 2017/00212* (2013.01); *A61B 2017/00398* (2013.01); *A61B 2017/3405* (2013.01); *A61B 2034/104* (2016.02); *A61B 2034/105* (2016.02); *A61B 2034/107* (2016.02); *A61B 2034/2055* (2016.02); *A61B 2034/2068* (2016.02); *A61B 2034/2072* (2016.02); *A61B 2034/252* (2016.02); *A61B 2034/254* (2016.02); *A61B 2090/031* (2016.02); *A61B 2090/064* (2016.02); *A61B 2090/365* (2016.02); *A61B 2090/3945* (2016.02)

(58) Field of Classification Search
CPC ........ A61B 2034/252; A61B 2090/365; A61B 34/37; A61B 34/74; A61B 34/76; A61B 2034/105; A61B 90/36; A61B 2034/2068; A61B 2034/254; A61B 34/10; A61B 34/25; A61B 34/70; A61B 2034/2059; A61B 2017/00725; A61B 2034/102
See application file for complete search history.

(56) References Cited

U.S. PATENT DOCUMENTS

| | | | |
|---|---|---|---|
| 4,979,949 A * | 12/1990 | Matsen, III | ............ A61B 17/15 606/53 |
| 5,046,375 A | 9/1991 | Salisbury et al. | |
| 5,078,140 A * | 1/1992 | Kwoh | ............ A61B 34/30 378/20 |
| 5,086,401 A | 2/1992 | Glassman et al. | |
| 5,142,930 A | 9/1992 | Allen et al. | |
| 5,154,717 A | 10/1992 | Matsen et al. | |
| 5,207,114 A | 5/1993 | Salisbury et al. | |
| 5,230,338 A | 7/1993 | Allen et al. | |
| 5,236,432 A | 8/1993 | Matsen et al. | |
| 5,299,288 A | 3/1994 | Glassman et al. | |
| 5,343,385 A | 8/1994 | Joskowicz et al. | |
| 5,388,480 A | 2/1995 | Townsend | |
| 5,399,951 A | 3/1995 | Lavallee et al. | |
| 5,402,801 A | 4/1995 | Taylor | |
| 5,408,409 A | 4/1995 | Glassman et al. | |
| 5,445,144 A | 8/1995 | Wodicka et al. | |
| 5,445,166 A | 8/1995 | Taylor | |
| 5,452,941 A | 9/1995 | Halse et al. | |
| 5,551,429 A | 9/1996 | Fitzpatrick et al. | |
| 5,572,999 A | 11/1996 | Funda et al. | |
| 5,576,727 A * | 11/1996 | Rosenberg | ............ G01B 5/008 345/179 |
| 5,587,937 A | 12/1996 | Massie et al. | |
| 5,611,353 A | 3/1997 | Dance et al. | |
| 5,625,576 A | 4/1997 | Massie et al. | |
| 5,630,431 A | 5/1997 | Taylor | |
| 5,638,819 A | 6/1997 | Manwaring et al. | |
| 5,676,673 A | 10/1997 | Ferre et al. | |
| 5,682,886 A | 11/1997 | Delp et al. | |
| 5,688,280 A | 11/1997 | Booth et al. | |
| 5,694,013 A | 12/1997 | Stewart et al. | |
| 5,695,500 A | 12/1997 | Taylor et al. | |
| 5,701,140 A | 12/1997 | Rosenberg et al. | |
| 5,704,791 A | 1/1998 | Gillio | |
| 5,727,554 A | 3/1998 | Kalend et al. | |
| 5,766,016 A | 6/1998 | Sinclair et al. | |
| 5,769,640 A | 6/1998 | Jacobus et al. | |
| 5,792,147 A | 8/1998 | Evans et al. | |
| 5,799,055 A | 8/1998 | Peshkin et al. | |
| 5,806,518 A | 9/1998 | Mittelstadt | |
| 5,831,408 A | 11/1998 | Jacobus et al. | |
| 5,854,634 A | 12/1998 | Kroitor | |
| 5,855,553 A | 1/1999 | Tajima et al. | |
| 5,871,018 A | 2/1999 | Delp et al. | |
| 5,887,121 A | 3/1999 | Funda et al. | |
| 5,888,220 A | 3/1999 | Felt et al. | |
| 5,898,599 A | 4/1999 | Massie et al. | |
| 5,928,137 A | 7/1999 | Green | |
| 5,950,629 A | 9/1999 | Taylor et al. | |
| 5,976,156 A | 11/1999 | Taylor et al. | |
| 5,978,696 A | 11/1999 | Vomlehn et al. | |
| 5,980,535 A | 11/1999 | Barnett et al. | |
| 5,984,930 A | 11/1999 | Maciunas et al. | |
| 5,987,960 A | 11/1999 | Messner et al. | |
| 6,002,859 A | 12/1999 | DiGioia, III et al. | |
| 6,006,126 A | 12/1999 | Cosman | |
| 6,006,127 A | 12/1999 | Van Der Brug et al. | |
| 6,017,305 A | 1/2000 | Bonutti | |
| 6,033,415 A | 3/2000 | Mittelstadt et al. | |
| 6,084,587 A | 7/2000 | Tarr et al. | |
| 6,104,158 A | 8/2000 | Jacobus et al. | |
| 6,109,270 A | 8/2000 | Mah et al. | |
| 6,111,577 A | 8/2000 | Zilles et al. | |
| 6,113,395 A | 9/2000 | Hon | |
| 6,120,433 A * | 9/2000 | Mizuno | .................. A61B 34/70 600/102 |
| 6,147,674 A | 11/2000 | Rosenberg et al. | |
| 6,161,032 A | 12/2000 | Acker | |
| 6,188,728 B1 | 2/2001 | Hurst | |
| 6,191,796 B1 | 2/2001 | Tarr | |
| 6,205,411 B1 | 3/2001 | DiGioia, III et al. | |
| 6,219,032 B1 | 4/2001 | Rosenberg et al. | |
| 6,223,100 B1 | 4/2001 | Green | |
| 6,226,566 B1 | 5/2001 | Funda et al. | |
| 6,228,089 B1 | 5/2001 | Wahrburg | |
| 6,231,526 B1 | 5/2001 | Taylor et al. | |
| 6,233,504 B1 | 5/2001 | Das et al. | |
| 6,259,806 B1 | 7/2001 | Green | |
| 6,285,902 B1 | 9/2001 | Kienzle et al. | |
| 6,288,705 B1 | 9/2001 | Rosenberg et al. | |
| 6,292,174 B1 | 9/2001 | Mallett et al. | |
| 6,300,936 B1 | 10/2001 | Braun et al. | |
| 6,322,467 B1 | 11/2001 | Hook et al. | |
| 6,322,567 B1 | 11/2001 | Mittelstadt et al. | |

(56) References Cited

U.S. PATENT DOCUMENTS

| | | |
|---|---|---|
| 6,325,808 B1 * | 12/2001 | Bernard ............ A61B 17/0469 318/568.11 |
| 6,337,994 B1 | 1/2002 | Stoianovici et al. |
| 6,366,273 B1 | 4/2002 | Rosenberg et al. |
| 6,369,834 B1 | 4/2002 | Zilles et al. |
| 6,377,011 B1 | 4/2002 | Ben-Ur |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,393,340 B2 | 5/2002 | Funda et al. |
| 6,405,072 B1 | 6/2002 | Cosman |
| 6,405,158 B1 | 6/2002 | Massie et al. |
| 6,417,638 B1 | 7/2002 | Guy et al. |
| 6,421,048 B1 | 7/2002 | Shih et al. |
| 6,424,885 B1 | 7/2002 | Niemeyer et al. |
| 6,430,434 B1 | 8/2002 | Mittelstadt |
| 6,434,416 B1 | 8/2002 | Mizoguchi et al. |
| 6,443,894 B1 | 9/2002 | Sumanaweera et al. |
| 6,466,815 B1 | 10/2002 | Saito et al. |
| 6,468,265 B1 | 10/2002 | Evans et al. |
| 6,493,608 B1 | 12/2002 | Niemeyer |
| 6,494,039 B2 | 12/2002 | Pratt et al. |
| 6,499,488 B1 | 12/2002 | Hunter et al. |
| 6,533,737 B1 | 3/2003 | Brosseau et al. |
| 6,546,277 B1 | 4/2003 | Franck et al. |
| 6,547,782 B1 | 4/2003 | Taylor |
| 6,551,325 B2 | 4/2003 | Neubauer et al. |
| 6,552,722 B1 | 4/2003 | Shih et al. |
| 6,583,161 B1 | 6/2003 | Medina |
| 6,611,141 B1 | 8/2003 | Schulz et al. |
| 6,642,686 B1 | 11/2003 | Ruch |
| 6,665,554 B1 | 12/2003 | Charles et al. |
| 6,671,651 B2 | 12/2003 | Goodwin et al. |
| 6,674,916 B1 | 1/2004 | Deman et al. |
| 6,676,669 B2 | 1/2004 | Charles et al. |
| 6,690,964 B2 | 2/2004 | Bieger et al. |
| 6,692,485 B1 | 2/2004 | Brock et al. |
| 6,701,174 B1 | 3/2004 | Krause et al. |
| 6,702,821 B2 | 3/2004 | Bonutti |
| 6,704,694 B1 | 3/2004 | Basdogan et al. |
| 6,711,431 B2 | 3/2004 | Sarin et al. |
| 6,711,432 B1 | 3/2004 | Krause et al. |
| 6,748,819 B2 | 6/2004 | Maeguchi et al. |
| 6,750,877 B2 | 6/2004 | Rosenberg et al. |
| 6,757,582 B2 | 6/2004 | Brisson et al. |
| 6,770,078 B2 | 8/2004 | Bonutti |
| 6,778,850 B1 | 8/2004 | Adler et al. |
| 6,785,572 B2 | 8/2004 | Yanof et al. |
| 6,786,896 B1 | 9/2004 | Madhani et al. |
| 6,801,801 B1 | 10/2004 | Sati |
| 6,810,281 B2 | 10/2004 | Brock et al. |
| 6,816,148 B2 | 11/2004 | Mallett et al. |
| 6,831,640 B2 | 12/2004 | Shih et al. |
| 6,850,794 B2 | 2/2005 | Shahidi |
| 6,853,965 B2 | 2/2005 | Massie et al. |
| 6,859,661 B2 | 2/2005 | Tuke |
| 6,877,239 B2 | 4/2005 | Leitner et al. |
| 6,894,678 B2 | 5/2005 | Rosenberg et al. |
| 6,920,347 B2 | 7/2005 | Simon et al. |
| 6,985,133 B1 | 1/2006 | Rodomista et al. |
| 6,987,504 B2 | 1/2006 | Rosenberg et al. |
| 7,001,346 B2 | 2/2006 | White |
| 7,035,716 B2 | 4/2006 | Harris et al. |
| 7,039,866 B1 | 5/2006 | Rosenberg et al. |
| 7,104,996 B2 | 9/2006 | Bonutti |
| 7,131,073 B2 | 10/2006 | Rosenberg et al. |
| 7,168,042 B2 | 1/2007 | Braun et al. |
| 7,199,790 B2 | 4/2007 | Rosenberg et al. |
| 7,206,626 B2 | 4/2007 | Quaid, III |
| 7,206,627 B2 | 4/2007 | Abovitz et al. |
| 7,225,115 B2 | 5/2007 | Jones |
| 7,491,198 B2 | 2/2009 | Kockro |
| 7,605,800 B2 | 10/2009 | Rosenberg |
| 7,660,623 B2 | 2/2010 | Hunter et al. |
| 7,683,565 B2 | 3/2010 | Quaid et al. |
| 7,742,804 B2 | 6/2010 | Faul |
| 7,747,311 B2 | 6/2010 | Quaid, III |
| 7,774,044 B2 | 8/2010 | Sauer et al. |
| 7,831,292 B2 | 11/2010 | Quaid et al. |
| 7,947,050 B2 | 5/2011 | Lee et al. |
| 7,947,051 B2 | 5/2011 | Lee et al. |
| 7,974,677 B2 | 7/2011 | Mire et al. |
| 7,996,110 B2 | 8/2011 | Lipow et al. |
| 8,005,571 B2 | 8/2011 | Sutherland et al. |
| 8,010,180 B2 | 8/2011 | Quaid et al. |
| 8,109,942 B2 | 2/2012 | Carson |
| 8,287,522 B2 | 10/2012 | Moses et al. |
| 8,391,954 B2 | 3/2013 | Quaid, III |
| 8,571,628 B2 | 10/2013 | Kang et al. |
| 8,911,499 B2 | 12/2014 | Quaid et al. |
| 9,002,426 B2 | 4/2015 | Quaid et al. |
| 9,492,237 B2 | 11/2016 | Kang et al. |
| 2001/0002830 A1 | 6/2001 | Rahn et al. |
| 2001/0005815 A1 | 6/2001 | Rosenberg et al. |
| 2001/0034530 A1 | 10/2001 | Malackowski et al. |
| 2001/0036245 A1 | 11/2001 | Kienzle et al. |
| 2001/0037064 A1 | 11/2001 | Shahidi |
| 2001/0039422 A1 | 11/2001 | Carol et al. |
| 2001/0041838 A1 | 11/2001 | Holupka et al. |
| 2002/0038085 A1 | 3/2002 | Immerz |
| 2002/0062177 A1 | 5/2002 | Hannaford et al. |
| 2002/0082498 A1 | 6/2002 | Wendt et al. |
| 2002/0107521 A1 | 8/2002 | Petersen et al. |
| 2002/0107522 A1 | 8/2002 | Picard et al. |
| 2002/0108054 A1 | 8/2002 | Moore et al. |
| 2002/0120188 A1 | 8/2002 | Brock et al. |
| 2002/0133174 A1 | 9/2002 | Charles et al. |
| 2003/0069591 A1 | 4/2003 | Carson et al. |
| 2003/0112281 A1 | 6/2003 | Sriram et al. |
| 2003/0128187 A1 | 7/2003 | Strubbe |
| 2003/0208122 A1 | 11/2003 | Melkent et al. |
| 2003/0209096 A1 | 11/2003 | Pandey et al. |
| 2004/0012806 A1 | 1/2004 | Murata |
| 2004/0024311 A1 | 2/2004 | Quaid, III |
| 2004/0034282 A1 | 2/2004 | Quaid et al. |
| 2004/0034283 A1 | 2/2004 | Quaid |
| 2004/0034302 A1 | 2/2004 | Abovitz et al. |
| 2004/0102866 A1 | 5/2004 | Harris et al. |
| 2004/0106916 A1 | 6/2004 | Quaid et al. |
| 2004/0115606 A1 | 6/2004 | Davies |
| 2004/0127788 A1 | 7/2004 | Arata |
| 2004/0128026 A1 | 7/2004 | Harris et al. |
| 2004/0157188 A1 | 8/2004 | Luth et al. |
| 2004/0167654 A1 | 8/2004 | Grimm et al. |
| 2004/0171924 A1 | 9/2004 | Mire et al. |
| 2004/0236424 A1 | 11/2004 | Berez et al. |
| 2005/0001831 A1 | 1/2005 | Shih et al. |
| 2005/0013477 A1 | 1/2005 | Ratti et al. |
| 2005/0027397 A1 | 2/2005 | Niemeyer |
| 2005/0062738 A1 | 3/2005 | Handley et al. |
| 2005/0093821 A1 | 5/2005 | Massie et al. |
| 2005/0107801 A1 | 5/2005 | Davies et al. |
| 2005/0113677 A1 | 5/2005 | Davies et al. |
| 2005/0137599 A1 | 6/2005 | Masini |
| 2005/0154471 A1 | 7/2005 | Aram et al. |
| 2005/0165489 A1 | 7/2005 | Michelson |
| 2005/0197800 A1 | 9/2005 | Goodwin et al. |
| 2005/0203384 A1 | 9/2005 | Sati et al. |
| 2005/0203536 A1 | 9/2005 | Laffargue et al. |
| 2005/0203539 A1 | 9/2005 | Grimm et al. |
| 2005/0215879 A1 | 9/2005 | Chuanggui |
| 2005/0222830 A1 | 10/2005 | Massie et al. |
| 2006/0033707 A1 | 2/2006 | Rodomista et al. |
| 2006/0058616 A1 | 3/2006 | Marquart et al. |
| 2006/0084867 A1 | 4/2006 | Tremblay et al. |
| 2006/0098851 A1 | 5/2006 | Shoham et al. |
| 2006/0109266 A1 | 5/2006 | Itkowitz et al. |
| 2006/0133827 A1 | 6/2006 | Becouarn et al. |
| 2006/0142657 A1 | 6/2006 | Quaid et al. |
| 2006/0293598 A1 | 12/2006 | Fraser |
| 2007/0142751 A1 | 6/2007 | Kang et al. |
| 2007/0260140 A1 | 11/2007 | Solar et al. |
| 2007/0270685 A1 | 11/2007 | Kang et al. |
| 2008/0004632 A1 | 1/2008 | Sutherland et al. |

(56) References Cited

U.S. PATENT DOCUMENTS

| | | | |
|---|---|---|---|
| 2008/0004633 | A1 | 1/2008 | Arata et al. |
| 2008/0010705 | A1 | 1/2008 | Quaid et al. |
| 2008/0010706 | A1 | 1/2008 | Moses et al. |
| 2008/0058945 | A1 | 3/2008 | Hajaj et al. |
| 2009/0000626 | A1 | 1/2009 | Quaid et al. |
| 2009/0000627 | A1 | 1/2009 | Quaid et al. |
| 2009/0012531 | A1 | 1/2009 | Quaid et al. |
| 2009/0012532 | A1 | 1/2009 | Quaid et al. |
| 2009/0306499 | A1 | 12/2009 | Van Vorhis et al. |
| 2010/0137882 | A1 | 6/2010 | Quaid, III |
| 2010/0198219 | A1 | 8/2010 | McFarlin et al. |
| 2011/0082462 | A1 | 4/2011 | Suarez et al. |
| 2011/0082468 | A1 | 4/2011 | Hagag et al. |
| 2011/0082587 | A1 | 4/2011 | Ziaei et al. |
| 2011/0213383 | A1 | 9/2011 | Lee et al. |
| 2012/0109152 | A1 | 5/2012 | Quaid, III |
| 2012/0176306 | A1 | 7/2012 | Lightcap et al. |
| 2013/0053648 | A1 | 2/2013 | Abovitz et al. |
| 2013/0096573 | A1 | 4/2013 | Kang et al. |
| 2013/0096574 | A1 | 4/2013 | Kang et al. |

FOREIGN PATENT DOCUMENTS

| | | |
|---|---|---|
| EP | 1 184 684 A2 | 3/2002 |
| EP | 1 380 266 A1 | 1/2004 |
| EP | 1 574 186 | 6/2008 |
| JP | 08-215211 A | 8/1996 |
| JP | 09-330016 A | 12/1997 |
| JP | 2000-279425 A | 10/2000 |
| JP | 2002-102251 | 4/2002 |
| JP | 2003-053684 | 2/2003 |
| JP | 2004-513684 | 5/2004 |
| WO | WO-95/01757 A1 | 1/1995 |
| WO | WO-96/17552 A1 | 6/1996 |
| WO | WO-00/35336 A2 | 6/2000 |
| WO | WO-02/00131 A1 | 1/2002 |
| WO | WO-02/24051 A2 | 3/2002 |
| WO | WO-02/060653 A2 | 8/2002 |
| WO | WO-02/061371 A1 | 8/2002 |
| WO | WO-02/061688 | 8/2002 |
| WO | WO-03/007101 | 1/2003 |
| WO | WO-03/077101 A2 | 9/2003 |
| WO | WO-03/077101 A3 | 9/2003 |
| WO | WO-2004/069036 A2 | 8/2004 |
| WO | WO-2004/069040 A2 | 8/2004 |
| WO | WO-2004/069041 A2 | 8/2004 |
| WO | WO-2004/070573 A2 | 8/2004 |
| WO | WO-2004/070577 A1 | 8/2004 |
| WO | WO-2004/070580 A2 | 8/2004 |
| WO | WO-2004/070581 A2 | 8/2004 |
| WO | WO-2004/075987 A1 | 9/2004 |
| WO | WO-2005/009215 A2 | 2/2005 |
| WO | WO-2005/072629 A1 | 8/2005 |
| WO | WO-2005/091220 A1 | 9/2005 |
| WO | WO-2005/120380 A1 | 12/2005 |
| WO | WO-2005/122916 A1 | 12/2005 |
| WO | WO-2006/004894 A2 | 1/2006 |
| WO | WO-2006/004894 A3 | 1/2006 |
| WO | WO-2006/091494 A1 | 8/2006 |
| WO | WO-2007/117297 A2 | 10/2007 |

OTHER PUBLICATIONS

U.S. Appl. No. 10/357,197, filed Feb. 21, 2006, Quaid et al.
U.S. Appl. No. 10/384,072, filed Mar. 6, 2003, Quaid, III.
U.S. Appl. No. 10/384,077, filed Mar. 6, 2003, Abovitz et al.
U.S. Appl. No. 10/384,078, filed Mar. 6, 2003, Quaid, III.
U.S. Appl. No. 10/384,194, filed Mar. 6, 2003, Quaid, III.
U.S. Appl. No. 10/621,119, filed Jul. 16, 2003, Quaid et al.
U.S. Appl. No. 11/646,204, filed Dec. 27, 2006, Kang et al.
U.S. Appl. No. 11/750,815, filed May 18, 2007, Kang et al.
U.S. Appl. No. 11/750,840, filed May 18, 2007, Quaid et al.
U.S. Appl. No. 12/144,496, filed Jun. 23, 2008, Quaid et al.
U.S. Appl. No. 12/144,507, filed Jun. 23, 2008, Quaid et al.
U.S. Appl. No. 12/144,517, filed Jun. 23, 2008, Quaid et al.
U.S. Appl. No. 12/144,526, filed Jun. 23, 2008, Quaid et al.
U.S. Appl. No. 12/698,353, filed Feb. 2, 2010, Quaid, III.
Abovitz et al., "The Future Use of Networked Haptic Learning Information Systems in Computer-Assisted Surgery," CAOS 2001, Jul. 6-8, 2001, pp. 337-338.
Abovitz, "Digital surgery: the future of medicine and human-robot symbiotic interaction," Industrial Robot: An International Journal, Oct. 2001, vol. 28, Issue 5, pp. 401-406 (abstract only).
Abovitz, "Human-Interactive Medical Robotics," CAOS 2000, Jun. 15-17, 2000, pp. 71-72.
Abovitz, "Human-Interactive Medical Robotics," CAOS 2001, Jul. 6-8, 2001, pp. 81-82.
Acosta, et al., "Development of a Haptic Virtual Environment", Computer-Based Medical Systems, Proceedings 12th IEEE Symposium. pp. 35-39, 1999.
Bainville, et al., Concepts and Methods of Registration for Computer-Integrated Surgery, Computer Assisted Orthopedic Surgery (CAOS), 1999, Hogrefe & Huber Publishers, 22 pages.
Bennett et al., "Autonomous Calibration of Single-Loop Kinematic Chains Formed by Manipulators With Passive End-Point Constraints," IEEE Transactions on Robotics and Automation, vol. 7, pp. 597-606, 1991.
Bettini et al., "Vision assisted control for manipulation using virtual fixtures: Experiments at macro and micro scales," in Proc. 2002 IEEE Intl. Conf. on Robotics and Automation, (Washington, DC), May 2002, 8 pages.
Burghart, et al., Robot Controlled Osteotomy in Craniofacial Surgery, 1st International Workshop on Haptic Devices in Medical Applications Proceedings, Institute for Process Control and Robotics, Jun. 23, 1999, 13 pages.
Chapter II Demand and Response to Written Opinion for PCT/US2006/005700, dated Dec. 15, 2006, 16 pages.
Chapter II Demand and Response to Written Opinion for PCT/US2006/049216, dated Jul. 15, 2008, 19 pages.
Chen et al., "Force Feedback for Surgical Simulation," Proceedings of the IEEE, New York, US, vol. 86, No. 3, Mar. 1, 1998. pp. 524-530.
Cobb et al., "A robotic system for TKR surgery," in Third Annual North American Program on Computer Assisted Orthopaedic Surgery, (Pittsburgh, PA), pp. 70-74, Jun. 1999.
Colgate et al., "Cobots: Robots for Collaboration with Human Operators", Department of Mech. Engineering Northwestern University, Mar. 1999.
Colgate, J. Edward, et al., "Cobots: Robots for Collaboration with Human Operators," proceedings of International Mechanical Engineering Congress & Exhibition, DSC-vol. 58, 1996, pp. 433-439.
Communication pursuant to Article 94(3) EPC for EP Application No. 06850614.6, dated Mar. 15, 2017, 3 pages.
Davies et al., "Acrobot-using Robots and Surgeons Synergistically in Knee Surgery", 1997 British Crown Copyright, pp. 173-178.
Davies et al., "The use of force control in robot assisted knee surgery," in Proceedings of the First Annual Symposium on Medical Robotics and Computer Assisted Surgery, vol. 2, (Pittsburgh, PA), pp. 258-262, Sep. 1994.
Davies, B., Computer-assisted and robotics surgery, International Congress and Symposium Series No. 223, 1997, Royal Society of Medicine Press Limited, 12 pages.
English translation of first Office Action for corresponding Chinese Application No. 200680012488.3, dated Jan. 15, 2010 (6 pages).
English translation of Office Action for Chinese Application No. 200480023380.5, dated Jan. 23, 2009 (7 pages).
English translation of Office Action for Chinese Application No. 200480023380.5, dated Jul. 4, 2008 (5 pages).
English translation of Office Action for Japanese Application No. 2006-520381, dated May 19, 2010 (5 pages).
English translation of Office Action for Japanese Application No. 2006-520381, dated Nov. 18, 2010 (5 pages).
Examination report for EP 04757075.9, dated Jan. 12, 2011, 5 pages.
Extended European Search Report for EP Application No. 18193075.1, dated Mar. 20, 2019, 7 pages.

(56) References Cited

OTHER PUBLICATIONS

Extended European Search Report for EP Application No. 19176645. 0, dated Sep. 20, 2019, 7 pages.
Final Office Action on U.S. Appl. No. 15/431,542 dated Jan. 30, 2018.
Fritz, et al., "Design of a Haptic Data Visualization System for People with Visual Impairments", IEEE Trans. on Rehabiliation Engineering, vol. 7, No. 3, Sep. 1999, 13 pages.
Goswami, et al., "Identifying Robot Parameters Using Partial Pose Information," IEEE Control Systems Magazine, vol. 13, No. 5, Oct. 1993, 11 pages.
Harris, et al., Experiences with Robotic Systems for Knee Surgery, CVR Med-MRCAS'97 Proceedings of the First Joint Conference on Computer Vision, Virtual Realty, and Robotics in Medicine and Medial Robotics and Computer-Assisted Surgery, Mar. 1997, Springer, 11 pages.
Ho, S.C. et al., "Robot Assisted Knee Surgery Establishing a Force Control Strategy Incorporating Active Motion Constraint," IEEE Engineering in Medicine and Biology Magazine, vol. 14, No. 3, May 1, 1995, col. 2-3, p. 293.
Hollerbach, J.M. & D. E. Johnson. Virtual Environment Rendering. To appear in Human and Machine Haptics, M. Cutkosky, R. Howe, K. Salisbury, and M. Srinivasan (eds.), MIT Press, 2000 (available at http://www.cs.ubc.ca/labs/spin/publications/related/hollerbach00. pdf), 25 pages.
International Preliminary Examination Report for PCT/US2003/007063, dated Sep. 2, 2004 (2 pages).
International Preliminary Report on Patentability for PCT/US2004/022978 including International Search Report and Written Opinion, dated Feb. 13, 2007 (6 pages).
International Preliminary Report on Patentability for PCT/US2006/005700, dated May 8, 2007 (7 pages).
International Preliminary Report on Patentability for PCT/US2006/049216, dated Sep. 10, 2008, 9 pages.
International Search Report and Written Opinion for corresponding PCT Application No. PCT/US2006/049216, dated May 8, 2008 (15 pgs.).
International Search Report and Written Opinion for PCT/US2006/005700, dated Jun. 27, 2006, 10 pages.
International Search Report for PCT/US2003/007063, dated Apr. 16, 2004 (7 pages).
Kanazides, Peter et al., "An Integrated System for Cementless Hip Replacement", Integrated Surgical Systems Department of Orthopedic Surgery, Sutter General Hospital, May/Jun. 1995, pp. 307-313.
Leeser et al., "Computerassisted teach and play: Novel user-friendly robot teach mode using gravity compensation and backdrivability," in Proceedings of the Robotics International/SME Fifth World Conference on Robotics Research, (Cambridge, MA), Sep. 1994, 7 pages.
Leeser, Karl, et al., "Control and Exploitation of Kinematic Redundancy in Torque-Controllable Manipulators via Multiple-Jacobian Superposition," to the International Conf. on Field & Service Robotics, Dec. 8-10, 1997, 7 pages.
London Press Services, "'Acrobot' capable of delicate knee surgery," Can. Med. Assoc. J., Jun. 15, 1997, 156(12), p. 1690.
Matsuoka, Yoky, et al., "Design of Life-Size Haptic Environments," Experimental Robotics VII, 2001, pp. 461-470.
Meggiolaro, et al., "Manipulator calibration using a single endpoint contact constraint," in 26th ASME Bienniel Mechanisms Conference, (Baltimore, MD), 2000, 9 pages.
Moore, Carl A., et al., "Cobot Implementation of 3D Virtual Surfaces," proceedings of the 2002 Institute of Electrical and Electronics Engineers International Conference on Robotics & Automation, May 2002, pp. 3242-3247.
Niki, et al., "Simple Haptic Display and Object Data Design", Proceedings of the 2000 IEEE/RSJ International Conference on Intelligent Robots and Systems, pp. 967-972, 2000.
Office Action for Chinese Application No. 200480023380.5, dated Jan. 23, 2009 (5 pages).
Office Action for Chinese Application No. 200480023380.5, dated Jul. 4, 2008 (4 pages).
Office Action for Japanese Application No. 2006-520381, dated May 19, 2010 (3 pages).
Office Action for Japanese Application No. 2006-520381, dated Nov. 18, 2010 (3 pages).
Otmane, S., et al., "Active Virtual Guides as an Apparatus for Augmented Reality Based Telemanipulation System on the Internet," presented at Institute of Electrical and Electronics Engineers Computer Society 33rd Annual Simulation Symposium ANSS 2000, held Apr. 16-20, 2000, pp. 185-191.
Park et al., "Virtual fixtures for robotic cardiac surgery," in Proc. Medical Image Computing and Computer-Assisted Intervention, (Utrecht, Netherlands), Oct. 2001, 2 pages.
Patent Abstracts of Japan for JP 08-215211 taken from website of Japanese Patent Office Apr. 28, 2011. (1 page).
Patent Abstracts of Japan for JP 2000-279425 and machine translation of JP 2000-279425 taken from website of Japanese Patent Office Apr. 28, 2011. (29 pages).
Patent Abstracts of Japan for JP 2002-102251 and machine translation of JP 2002-102251 taken from website of Japanese Patent Office Apr. 28, 2011. (10 pages).
Patent Abstracts of Japan for JP 2003-053684 from website of Japanese Patent Office (1 page).
Patent Abstracts of Japan for JP 2003-053684 taken from website of Japanese Patent Office Nov. 22, 2010. (1 page).
PCT/US2006/049216, Partial Intl. Search Report, dated Jan. 18, 2008 (2 pgs.).
Press Release, "The Acrobot Company Wins Best Surgical Innovation Award," Acrobot Precision Surgical Systems, May 24, 2002, 1 page.
Quaid et al., "Haptic Information Displays for Computer-Assisted Surgery," Proceedings of the 2002 IEEE International Conference on Robotics & Automation, May 2002, pp. 2092-2097.
Quaid, Arthur E., et al., "FGS WAM: First Cadaver Trial," Z-Kat, Inc. Confidential Material, Sep. 28, 2001, pp. 1-7.
Quaid, Arthur E., et al., "FGS WAM: Integration of Fluorotactic Guidance with the Whole-Arm Manipulator," Z-Kat, Inc. Confidential Material, Dec. 28, 2000, pp. 1-6.
Quaid, et al., "The Use of Haptic Information Displays for Assisting in the Execution of Image-Guided Surgery Plans," Syllabus of the Computer Assisted Orthopaedic Surgery Meeting, Jul. 2001, pp. 338-340.
Roche, "Changing the way surgeons plan and execute minimally invasive unicompartmental knee surgery," Orthopaedic Product News, pp. 16-18, Jul./Aug. 2006.
Rosenberg, "Virtual Fixtures: Perceptual Tools for Telerobotic Manipulation", 1993 IEEE, 76-82.
Rosenberg, Virtual Fixtures: Perceptual overlays enhance operator performance in telepresence tasks. PhD thesis, Stanford University, Aug. 1994, 7 pages.
Sayers, Craig P., et al., "An Operator Interface for Teleprogramming Employing Synthetic Fixtures," to appear in Presence, Special Issue on Networked Virtual Environments and Teleoperation, Jun. 1994, pp. 1-27.
Schneider et al., "A six-degree-of-freedom passive arm with dynamic constraints (PADyC) for Cardiac Surgery Application: Preliminary Experiments". Computer Aided Surgery, 2001.
Schneider, O., et al., "Synergistic Robotic Assistance to Cardiac Procedures," presented to Computer Assisted Radiology and Surgery on Jun. 23-26, 1999, 5 pages.
Second Office Action and English translation for corresponding Chinese Application No. 200680012488.3, dated Oct. 12, 2010 (10 pages).
Sensable Technologies, Inc., "Freeform Feel the Difference", 2001, 4 pages.
Sensable Technologies, Inc., "FreeForm Modeling—Technical Features," 2003, 2 pages.
Steines et al., Segmentation of Osteoarthritic Femoral Cartilage Using Live Wire, Proc. Intl. Soc. Mag. Reson. Med. 8, 2000, 1 page.
Taylor et al., An Image-Directed Robotic System for Precise Orthopedic Surgery, 1994, 15 Pages.

(56) References Cited

OTHER PUBLICATIONS

Taylor, Russell et al., "An Image-Directed Robotic System for Precise Orthopaedic Surgery", IEEE Transactions on Robotics and Automation, vol. 10, No. 3, Jun. 1994, pp. 261-275.

Taylor, Russell et al., "Redundant Consistency Checking in a Precise Surgical Robot", Annual International Conference of the IEEE Engineering in Medicine and Biology Society, vol. 12, No. 5, 1990, pp. 1933-1935.

Taylor, Russell et al., "Robotic Joint Replacement Surgery", NSF Engineering Research Center for Computer-Integrated Surgical Systems and Technology, 2000, 2001, 2004, 71 pages.

Tognetti, Lawrence Joseph, "Actuator Design for a Passive Haptic Display," Georgia Institute of Technology, Jun. 1999, 33 pages.

Townsend et al., "Teleoperator slave—WAM design methodology," Industrial Robot, vol. 26, No. 3, pp. 167-177, 1999.

U.S. Office Action on U.S. Appl. No. 15/431,542 dated Aug. 9, 2017.

World Wide Web, http://haptics.me.jhu.edu/r.sub.--hapt.html, "Haptic Interfaces and Virtual Environments," printed on Jun. 12, 2003, 2 pages.

World Wide Web, http://haptics.me.jhu.edu/r.sub.--kine.html, "Robot Design and Kinematics," printed on Jun. 12, 2003, 2 pages.

World Wide Web, http://www.acrobot.co.uk/background.html, "The Acrobot Company Limited—Background," printed on Jul. 10, 2002, 1 page.

World Wide Web, http://www.acrobot.co.uk/home.html, "The Acrobot Company Limited—Precision Surgical Systems," printed on Jul. 10, 2002, 1 page.

World Wide Web, http://www.acrobot.co.uk/meetings.html, "The Acrobot Company Limited—Meetings and Publications," printed on Jul. 10, 2002, pp. 1-3.

World Wide Web, http://www.acrobot.co.uk/products.html, "The Acrobot Company Limited—Products," printed on Jul. 10, 2002, pp. 1-6.

World Wide Web, http://www.fcs-cs.com/robotics/content/assistance.htm, "Surgical Assistance," printed on Jun. 12, 2003, 1 page.

World Wide Web, http://www.fcs-cs.com/robotics/content/design.htm, "Virtual Design, Assembly & Maintenance," printed on Jun. 12, 2003, 1 page.

World Wide Web, http://www.fcs-cs.com/robotics/content/endeffectors.htm, "End effectors," printed on Jun. 12, 2003, 1 page.

World Wide Web, http://www.fcs-cs.com/robotics/content/hapticmaster.htm, "HapticMASTER", printed on Jun. 12, 2003, 1 page.

World Wide Web, http://www.fcs-cs.com/robotics/content/reality.htm, "Virtual Reality," printed on Jun. 12, 2003, 1 page.

World Wide Web, http://www.fcs-cs.com/robotics/content/rehabilitation.htm, "Rehabilitation," printed on Jun. 12, 2003, 1 page.

World Wide Web, http://www.fcs-cs.com/robotics/content/research.htm, "Research," printed on Jun. 12, 2003, 1 page.

World Wide Web, http://www.fcs-cs.com/robotics/content/simulation.htm, "Simulation & Training," printed on Jun. 12, 2003, 1 page.

World Wide Web, http://www.fcs-cs.com/robotics/content/software.htm, "Software," printed on Jun. 12, 2003, 1 page.

World Wide Web, http://www.merl.com/projects/surgSim99/, "Knee Arthroscopy Simulation," printed on Jun. 12, 2003, 2 pages.

Written Opinion for PCT/US2006/049216, dated May 8, 2008, 12 pages.

Zilles, et al., "A Constraint-Based God-object Method for Haptic Display", IEEE Proceedings, pp. 146-151, 1995.

Schneider et al., "A-six-degree-of-freedom passive arm with dynamic constraints (PADyC) for Cardiac Surgery Application: Preliminary Experiments", Computer Aided Surgery; Year 2001, 13 Pages.

* cited by examiner

ROBOTICALLY-ASSISTED CONSTRAINT MECHANISM

CROSS-REFERENCE TO RELATED PATENT APPLICATIONS

This application is a continuation of U.S. application Ser. No. 15/431,542, filed Feb. 13, 2017, which is a continuation of U.S. application Ser. No. 13/347,330, filed Jan. 10, 2012, which is a continuation of U.S. application Ser. No. 10/384,078, filed Mar. 6, 2003, which claims the benefit of and priority to U.S. Provisional Application No. 60/362,368, filed Mar. 6, 2002, all of which are hereby incorporated by reference herein in their entireties. The following applications are also incorporated herein by reference: U.S. application Ser. No. 10/384,077 filed Mar. 6, 2003, entitled "System And Method For Intra-Operative Haptic Planning of a Medical Procedure"; U.S. application Ser. No. 10/384,072 filed Mar. 6, 2003, entitled "System And Method For Haptic Sculpting Of Physical Objects"; and U.S. application Ser. No. 10/384,194 filed Mar. 6, 2003, entitled "System And Method For Interactive Haptic Positioning Of A Medical Device."

BACKGROUND OF THE INVENTION

The present invention relates generally to computer-assisted surgery systems and surgical navigation systems, and more particularly to a system and method for using a surgical tool as an input device during a medical procedure.

The functions of a computer-assisted surgery (CAS) system may include pre-operative planning of a procedure, presenting pre-operative diagnostic information and images in useful formats, presenting status information about a procedure as it takes place, and enhancing performance. The CAS system may be used for procedures in traditional operating rooms, interventional radiology suites, mobile operating rooms or outpatient clinics. Many approaches to CAS have been attempted commercially. The procedure may be any medical procedure, whether surgical or non-surgical.

Navigation systems are used to display the positions of surgical tools with respect to pre- or intraoperative image datasets. These images include intraoperative images, such as two-dimensional fluoroscopic images, and preoperative three dimensional images generated using, for example, magnetic resonance imaging (MM), computer tomography (CT) and positron emission tomography (PET). The most popular navigation systems make use of a tracking or localizing system. These systems locate markers attached or fixed to an object, such as an instrument or a patient, and track the position of markers. These tracking systems are optical and magnetic, but also include acoustic systems. Optical systems have a stationary stereo camera pair that observes passive reflective markers or active infrared LEDs attached to the tracked tools. Magnetic systems have a stationary field generator that emits a magnetic field that is sensed by small coils integrated into the tracked tools. These systems are sensitive to nearby metal objects.

While navigation systems are relatively easy to integrate into the operating room, a fundamental limitation is that they have restricted means of communication with the surgeon. Most systems transmit information to the surgeon via a computer monitor. Conversely, the surgeon transmits information to the system via a keyboard and mouse, touch-screen, voice commands, control pendant, or foot pedals, and also by moving the tracked tool. The visual displays of navigation systems may at best display multiple slices through three-dimensional diagnostic image datasets, which are not easy to interpret for complex 3-D geometries. These displays also require the surgeon to focus his visual attention away from the surgical field.

When defining a plan using a tracked tool, it can be difficult to simultaneously position the tool appropriately in multiple degrees of freedom (DOFs). Similarly, when aligning a tracked instrument with a plan, it is difficult to control the position of the tool in multiple simultaneous DOFs, especially where high-accuracy is desirable. It is perhaps not a coincidence that navigation systems have had their largest acceptance in cranial neurosurgery, where most applications involve specifying a trajectory to a feature of interest without hitting critical features. Often, the tip of the tool is pressed against the anatomy and pivoted, effectively decoupling the position and orientation planning of the trajectory.

Autonomous robots have been applied commercially to joint replacement procedures. These systems make precise bone resections, improving implant fit and placement relative to techniques that rely on manual instruments. Registration is performed by having the robot touch fiducial markers screwed into the bones or a series of points on the bone surfaces. Cutting is performed autonomously with a high-speed burr, although the surgeon can monitor progress and interrupt it if necessary. Bones must be clamped in place during registration and cutting, and are monitored for motion, which then requires re-registration. Deficiencies reported by users of these systems include the large size of the robot, poor ergonomics, the need for rigidly clamping the bone for the 45-60 minutes required for registration and cutting, and the need for increasing the incision by 50-100 mm to provide adequate access for the robot. Furthermore, autonomous robots generally function best in highly structured environments, as evidenced by the rigid clamping of the bones of interest and making larger incisions to keep soft tissue away from the robot.

Except for specific steps of some surgical procedures, modern surgeries do not tend to provide well-structured environments for autonomous robots. A robot is generally not able to keep track of the surgical staff and instrumentation required to support a procedure. Although strict management of the operating environment might make this possible, the complexity of the human body will always provide a high degree of unstructuredness.

Robotic technology can also be used to improve upon standard practice without requiring autonomous operation. Notable commercial systems of this type include teleoperated robotic systems for laproscopic surgeries ranging from gall-bladder removal to closed-chest beating heart coronary surgery. These systems provide a console for the surgeon that includes a high-fidelity display and a master input device. The slave robot is coupled to the master and physically interacts with the anatomy. The benefits of these systems are primarily in providing an ergonomic working environment for the surgeon while improving dexterity through motion scaling and tremor reduction. Although the master console would normally be in the same room as the patient, an interesting byproduct of these systems is that they enable telesurgery. However, the robots have minimal autonomy in these systems, which is not surprising given the complexity involved in manipulating and altering soft tissue.

SUMMARY OF THE INVENTION

One aspect of a preferred embodiment of the invention generally pertains to use of robotic devices, preferably haptic devices, as an input device, allowing information to pass from the user to a computer-assisted surgery system. When used as an input device, a haptic device may be used for defining anatomical reference geometry, manipulating the position and/or orientation of virtual implants, manipulating the position and/or orientation of surgical approach trajectories, manipulating the positions and/or orientation of bone resections, and the selection or placement of any other anatomical or surgical feature. The haptic device may also be used for more generic user interface functions, including but not limited to, moving a cursor, selecting buttons or other similar user interface objects, selecting pull-down menus, manipulating on-screen dials, knobs, and other controls. When in this user-input mode the haptic device can be constrained to move in only certain directions which may be defined relative to the position of a predetermined portion of the haptic device, relative to the position of the patient or a portion of the patient anatomy, or relative to images or 3-D models of schematic, virtual, atlas, or actual patient anatomical features.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE DRAWINGS

Figure 1:
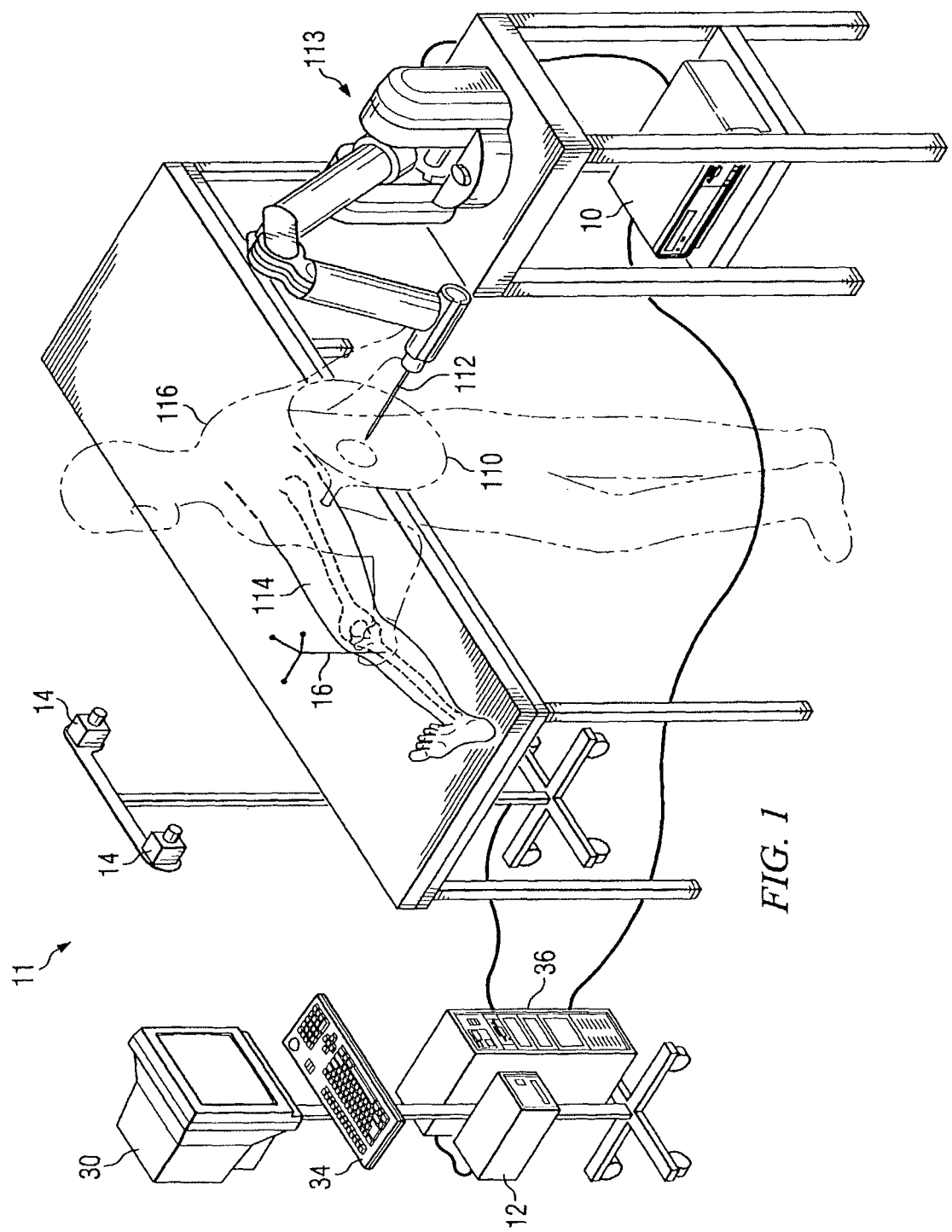
FIG. 1 is a diagrammatic illustration of an exemplary operating room in which a haptic device is used with a computer-assisted surgery system.

In the following description, like numerals refer to like elements. References to "surgeon" include any user of a computer-assisted surgical system, a surgeon being typically a primary user. References to "surgical procedure" include any medical procedure, whether interventional or non-interventional, an interventional procedure being typically the primary procedure.

A haptic device is a mechanical or electromechanical device that interacts and communicates with a user, such as a surgeon, using sensory information such as touch, force, velocity, position, and/or torque. Some robots may be used as haptic devices, though haptic devices may include devices that are not necessarily considered to be robots in a conventional sense. Haptic devices typically have little autonomy.

In general, a component of interest may be optionally coupled to the haptic devices. A component of interest may comprise a medical device, for example a surgical tool, a microscope, a laser range finder, a camera, a surgical light, an endoscope, an ultrasound probe, a radiotherapy device, interventional medical tools, rehabilitative systems for physical therapy, and/or the like. The terms "medical device", "surgical device" and "surgical tool" are used interchangeably herein.

For example, when used during surgery, such devices cooperatively hold a surgical instrument in conjunction with the surgeon. The surgeon moves the surgical instrument with the assistance of, or input from, the haptic device. Alternatively, in a teleoperation system, the haptic device may exclusively hold the surgical instrument. In such an implementation, the surgeon moves a "master" haptic device that is coupled to a "slave" device in order to interactively manipulate the surgical tool. In a teleoperation system, the master haptic device may be physically separated from the surgical site to provide a more ergonomic or immersive working position for the surgeon and/or allow the surgeon to perform the surgery remotely. In an impedance mode, a haptic device measures or senses the pose (position, orientation, velocity, and/or acceleration) of the surgical instrument and applies forces and/or torques ("wrench") to the instrument. In an "admittance" mode, a haptic device measures the wrench at some location on the device (or surgical instrument) and acts to modify the position of the instrument. There may be a static, quasi-static, or dynamic mapping between the sensed pose and output wrench. Common mappings may include wrenches that result from the tool interacting with "virtual" objects defined by or with input from a user, which may include mathematical or simulated mechanical constraints.

A "haptic object" is used herein to describe such a mapping. In some cases, a haptic object may only produce non-zero outputs for certain joint angles of the haptic device, or only for certain endpoint positions and/or orientations of the haptic device. A haptic object may be a smoothly time varying mapping and/or may only exist for certain times. A haptic object may have an associated spatial or geometric representation that corresponds to locations where the mapping is discontinuous or has other properties that can be felt by the user when interacting with the haptic object. For example, if a haptic object only produces non-zero outputs when the endpoint of the haptic device lies within a spherical region in space, then it may be useful to present a corresponding spherical representation to the user. However, a haptic object may not necessarily have such a clearly defined boundary or similar internal structures. A haptic object may be active over the entire range of endpoint positions, endpoint orientations, and/or joint positions of the haptic device or only a portion of these ranges. There may be multiple haptic objects active at any given time, possibly in overlapping portions of space.

A "haptic cue" is used to describe an aspect of the mapping of a haptic object. Having a cue may convey information or produce a desired effect when the user interacts with the haptic object. Haptic cues and haptic objects do not necessarily correspond to user interface or software programming components in a particular embodiment and may be simply one of many ways to design, implement, present to the user the mappings between the inputs and outputs of the haptic device.

The reduction or elimination of autonomy increases the comfort level of users, such as surgeons. Any time a robot moves autonomously, the surgeon is no longer in control and must simply observe the robot's progress. Robot motions have to be slow to provide adequate time for the surgeon to respond should something unusual happen. If, however, a robot acts, at least mostly, in a passive manner, even if capable of active motions, then the surgeon does not cede control to the robot.

Using a device capable of active motions in such a way that it only acts like a passive device from the user's perspective has advantages. Active actuators can be used to counteract the effect of gravity, allowing a greater variety of mechanism designs. The device can be used in an autonomous mode for performing automated testing and service procedures.

FIG. 1 is a diagrammatic illustration of an exemplary operating room in which a haptic device 113 is used with a computer-assisted surgery system 11. Computer-assisted surgery system 11 comprises a display device 30, an input device 34, and a processor based system 36, for example a computer. Input device 34 may be any input device now known or later developed, for example, a keyboard, a mouse, a trackball, and/or the like. Display device 30 may be any display device now known or later developed for displaying two-dimensional and/or three-dimensional images, for example a monitor, a wearable display, a projection display, a head-mounted display, stereoscopic views, a display device capable of displaying image(s) projected from an image projecting device, for example a projector, and/or the like. If desired, display device 30 may be a display device capable of displaying a holographic image. If desired, display device 30 may be a touch screen and be used as an input device.

Haptic device 113 is, in the illustrated example, a robotic device. Haptic device 113 may be controlled by a processor based system, for example a computer 10. Computer 20 may also include power amplification and input/output hardware. Haptic device 113 may communicate with computer-assisted surgery system 11 by any communication mechanism now known or later developed, whether wired or wireless.

Also shown in FIG. 1 is a storage medium 12 coupled to processor based system 36. Storage medium 12 may accept a digital medium which stores software and/or other data. A surgical tool or instrument 112 is shown coupled to haptic device 113. Surgical tool 112 is preferably mechanically coupled to haptic device 113, such as by attaching or fastening it. However, if desired, surgical tool 112 may be coupled, either directly or indirectly, to haptic device 113 by any other method, for example magnetically. If desired, vacuum may be used to couple surgical tool 112 to haptic device 113. Surgical tool 112 may be haptically controlled by a surgeon remotely or haptically controlled by a surgeon 116 present in proximity to surgical tool 112.

Haptic object 110 is a virtual object used to guide and/or constrain the movement and operations of surgical tool 112 to a target area inside a patient's anatomy 114, for example the patient's leg. In this example, haptic object 110 is used to aid the surgeon to target and approach the intended anatomical site of the patient. Haptic feedback forces are used to slow and/or stop the surgical tool's movement if it is detected that a portion of surgical tool 112 will intrude or cross over predefined boundaries of the haptic object. Furthermore, haptic feedback forces can also be used to attract (or repulse) surgical tool 112 toward (or away from) haptic object 110 and to (or away from) the target. If desired, surgeon 116 may be presented with a representation of the anatomy being operated on and/or a virtual representation of surgical tool 112 and/or haptic object 110 on display 30.

When surgical tool 112 is haptically controlled by a surgeon remotely, for example when conducting a teleoperation, the surgeon controls the movement of the surgical tool using the master haptic device and/or a real or simulated display of the surgical tool, patient anatomy, and/or additional haptic or visual objects designed to aid the surgical procedure. Haptic feedback forces may be transmitted by slave haptic device 113 to the surgeon at the remote location via the master haptic device to guide the surgeon. Alternatively, the haptic feedback forces may be generated at the master device and transmitted to the surgeon directly. In some cases either the slave or master device may be a positioning device with little or no haptic capabilities.

The CAS system preferably includes a localization or tracking system that determines or tracks the position and/or orientation of various trackable objects, such as surgical instruments, tools, haptic devices, patients, and/or the like. The tracking system continuously determines, or tracks, the position of one or more trackable markers disposed on, incorporated into, or inherently a part of the trackable objects, with respect to a three-dimensional coordinate frame of reference. Markers can take several forms, including those that can be located using optical (or visual), magnetic or acoustical methods. Furthermore, at least in the case of optical or visual systems, location of an object's position may be based on intrinsic features, landmarks, shape, color, or other visual appearances, that, in effect, function as recognizable markers.

Any type of tracking system may be used, including optical, magnetic, and/or acoustic systems, that may or may not rely on markers. Present day tracking systems are typically optical, functioning primarily in the infrared range. They usually include a stationary stereo camera pair that is focused around the area of interest and sensitive to infrared radiation. Markers emit infrared radiation, either actively or passively. An example of an active marker is a light emitting diodes (LEDs). An example of a passive marker is a reflective marker, such as ball-shaped marker with a surface that reflects incident infrared radiation. Passive systems require a an infrared radiation source to illuminate the area of focus. A magnetic system may have a stationary field generator that emits a magnetic field that is sensed by small coils integrated into the tracked tools.

With information from the tracking system on the location of the trackable markers, CAS system 11 is programmed to be able to determine the three-dimensional coordinates of an end point or tip of a tool and, optionally, its primary axis using predefined or known (e.g. from calibration) geometrical relationships between trackable markers on the tool and the end point and/or axis of the tool. A patient, or portions of the patient's anatomy, can also be tracked by attachment of arrays of trackable markers. In the illustrated example, the localizer is an optical tracking system that comprises one or more cameras 14 that preferably track a probe 16. As shown in FIG. 1, cameras 14 may be coupled to processor based system 36. If desired, cameras 14 may be coupled to computer 10. Probe 16 may be a conventional probe now known or later developed. If desired, the probe may be rigidly attached to haptic device 113 or integrated into the design of haptic device 113.

If desired, in an implementation, processor based system 36 may comprise a portion of image guided surgery software to provide minimal user functionality e.g., retrieval of previously saved surgical information, preoperative surgical planning, determining the position of the tip and axis of instruments, registering a patient and preoperative and/or intraoperative diagnostic image datasets to the coordinate system of the tracking system, etc. Image guided surgery using this method may not be possible with the computer alone. As such, full user functionality may be enabled by providing the proper digital medium to storage medium 12 coupled to computer 36. The digital medium may comprise an application specific software module. The digital medium may also comprise descriptive information concerning the surgical tools and other accessories. The application specific software module may be used to assist a surgeon with planning and/or navigation during specific types of procedures. For example, the software module may display predefined pages or images corresponding to specific steps or stages of a surgical procedure. At a particular stage or part of a module, a surgeon may be automatically prompted to perform certain tasks or to define or enter specific data that will permit, for example, the module to determine and display appropriate placement and alignment of instrumentation or implants or provide feedback to the surgeon. Other pages may be set up to display diagnostic images for navigation and to provide certain data that is calculated by the system for feedback to the surgeon. Instead of or in addition to using visual means, the CAS system could also communicate information in ways, including using audibly (e.g. using voice synthesis) and tactilely, such as by using a haptic interface of device. For example, in addition to indicating visually a trajectory for a drill or saw on the screen, a CAS system may feedback to a surgeon information whether he is nearing some object or is on course with an audible sound. To further reduce the burden on the surgeon, the module may automatically detect the stage of the procedure by recognizing the instrument picked up by a surgeon and move immediately to the part of the program in which that tool is used.

The software module may be such that it can only be used a predefined number of times. If desired, the software module functions only when used in conjunction with the portion of the image guided surgery software that resides on computer 36. The software which resides on computer 36 in conjunction with the software on the digital medium processes electronic medical diagnostic images, registers the acquired images to the patient's anatomy, and/or registers the acquired images to any other acquired imaging modalities, e.g., fluoroscopy to CT, MRI, etc. if desired, the image datasets may be time variant, i.e. image datasets taken at different times may be used. Media storing the software module can be sold bundled with disposable instruments specifically intended for the procedure. Thus, the software module need not be distributed with the CAS system. Furthermore, the software module can be designed to work with specific tools and implants and distributed with those tools and implants. Moreover, CAS system can be used in some procedures without the diagnostic image datasets, with only the patient being registered. Thus, the CAS system need not support the use of diagnostic images in some applications—i.e. an imageless application.

An example of the illustrated robotic arm is a robotic arm manufactured by Barrett Technology, and referred to as the "Whole-Arm Manipulator" or "WAM". This robotic arm has a cable transmission, which provides high bandwidth, back-drivability, and force fidelity. However, other robotic devices capable of impedance or admittance modes of haptic interaction could be used. For example, direct-drive systems or systems with other types of low-friction transmissions or systems with a combination of transmission types may also be well-suited to serve as a haptic device for surgical applications. Furthermore, the haptic device need not necessarily take the form of a robotic arm. The WAM robotic arm has a four degrees of freedom of movement. However, it is augmented by a 1-DOF direct-drive wrist for trajectory-based medical applications. If desired, degrees of freedom may be added or removed without affecting the scope of the illustrated invention.

Though it has some advantages, a cable transmission has some disadvantages. It requires careful installation and maintenance to prevent the possibility of failure during a procedure. Furthermore, a cable transmission is not as stiff as geared transmissions. Similar deficiencies may also be found in haptic devices using other types of transmissions.

These deficiencies may be addressed by augmenting existing position sensors that are mounted on drive motors with additional redundant sensors. These sensors may be of various types, including without limitation rotary encoders or resolvers, tilt sensors, heading (compass) sensors, sensors that detect the direction of gravity, an optical, magnetic or acoustical tracking system (such as optical camera systems of the type commonly used to track surgical instruments), or laser-based position sensing. The output of these sensors can be compared with the original sensors to detect discrepancies that may indicate problems in the transmissions or sensors. In addition, the added sensors can be used to detect both low bandwidth deflections in the cable transmissions, which the system can then easily compensate for using well-known control techniques. The sensor may also detect the high bandwidth deflections in the cable transmissions, which can provide an additional input to the servo loop and permit improved stability of the servo system, using well-known control techniques for systems that include sensors on both the drive and load sides of a transmission. The sensor can also improve the accuracy of the determination of the pose of the arm by reducing or eliminating the effect of deflections of the arm links and/or transmission. Such sensors could also be used to overcome similar deficiencies in robotic devices using other types of transmission systems.

When performing surgery, a haptic device capable of holding a tool, e.g. a drill guide or other similar constraint or attachment mechanism for surgical tools is positioned relative to the patient such that it can attain the poses appropriate for a variety of approaches for a particular procedure. It is also registered to the physical anatomy such that it can correlate information in diagnostic or planning image datasets, which can be two or three dimensional, to locations in physical space using well-known registration techniques. The image datasets may be one or more images generated using for example, magnetic resonance imaging (MM), computer tomography (CT), positron emission tomography (PET), magnetic resonance angiography (MRA), single photon emission computed tomography (SPECT), magnetic resonance venography (MRV), contrast enhanced MR venography (CEMRV), CT angiography, CT myelography, MR angiography, MR myelography, fluoroscopy, optical imaging, isotope imaging, ultrasound microscopy, laproscopic ultrasound, and MR spectrometry. Such images may include, for example, x-ray images, digital x-ray images, computer tomography images, MRI images, MRA images, MR spectrometric images, PET images, MRV images, SPECT images, CEMRV images, CT angiographic images; CT myelographic images, MR myelographic images, flair images, two-dimensional fluoroscopic images, three-dimensional fluoroscopic images, two-dimensional ultrasonic images, three-dimensional ultrasonic images, ultrasound microscopy images, laproscopic ultrasound images, optical images, isotopic images, laser depth maps, line arts, sketches, "cartoon" representations, holographic images, and/or the like.

Features to be avoided, such as blood vessels, tendons, nerves, and critical areas of the brain can be automatically, semi-automatically, or manually defined on the image datasets. Features targeted by the procedure, such as tumors, osteophytes, anatomical targets for deep-brain stimulation, biopsy sites, anatomical sites for implant placement, or other regions of the anatomy can also be automatically, semi-automatically, or manually defined on the image datasets.

The image dataset(s), coupled with definitions of features to be avoided, can be used to create haptic "cues" that indicate to the surgeon that a violation of sensitive anatomy is taking place. A general function of these types of cues is to apply forces and/or torques that tend to repulse the haptic device from poses where an instrument attached to the device would, for example, impact the defined critical features. Similarly, the image dataset(s), coupled with the definitions of features to be targeted can also used to create haptic cues that indicate to the surgeon that the desired target region would be reached by the surgical instrument appropriately attached to the haptic arm. A general function of these types of cues is to attract the haptic device to such poses or lock the haptic device into these poses once they are attained.

While the haptic device can be deployed as a fully integrated component of a computer-aided surgery system, there are advantages to having the haptic device act as an optional peripheral to such a system. The system is then convenient to use for procedures that do not require the use of the haptic device. There are also development and architectural advantages to this approach. The haptic device will likely require a real-time operating system or special motion control hardware to generate high-frequency updates for the haptic control system. The computer-aided surgery system will have different requirements, such as fast graphics processing hardware and compatibility requirements with a range of user input and output devices, so that there are advantages of having two computer systems to meet the differing uses. Separating the computer surgery and haptic arm components also has safety advantages. The haptic device therefore preferably contains only computing software and hardware that is necessary for ensuring high-performance, stable, and safe operation. The computer aided surgery system can contain software and hardware for connecting to a hospital network, displaying various graphical views, supporting various user input/output devices, managing libraries of implant and instrument databases, and/or any other functionality useful in such a system. This architecture also allows developers with minimal knowledge of haptic systems to build applications that use the haptic device. The physical interface between these two systems can be wired or wireless, such as a serial, USB, or other cable communications interface, or wireless ethernet, wireless serial, infra-red or other wireless communications system. The software interface between these systems would include a set of commands that allows the computer aided surgery system to control operation of the haptic device. For example, the computer-aided surgery system may send a command to the haptic device requesting it to enter into a joystick-like input mode with certain stiffness parameters. The haptic arm system checks if the parameters are safe and otherwise acceptable, and then enters into such a mode or responds with an appropriate error message. The computer-aided surgery system and haptic device may also be integrated into a single system unit, or may be implemented using a single or a multi-processor computing device. The CAS system, the haptic device and/or computer 10 may also be integrated into another piece of equipment, such as an imaging equipment (e.g., fluoroscopy, CT, MR, ultrasound, and/or the like), an equipment cart in the room where the medical procedure is performed, and/or the like.

Figure 2:
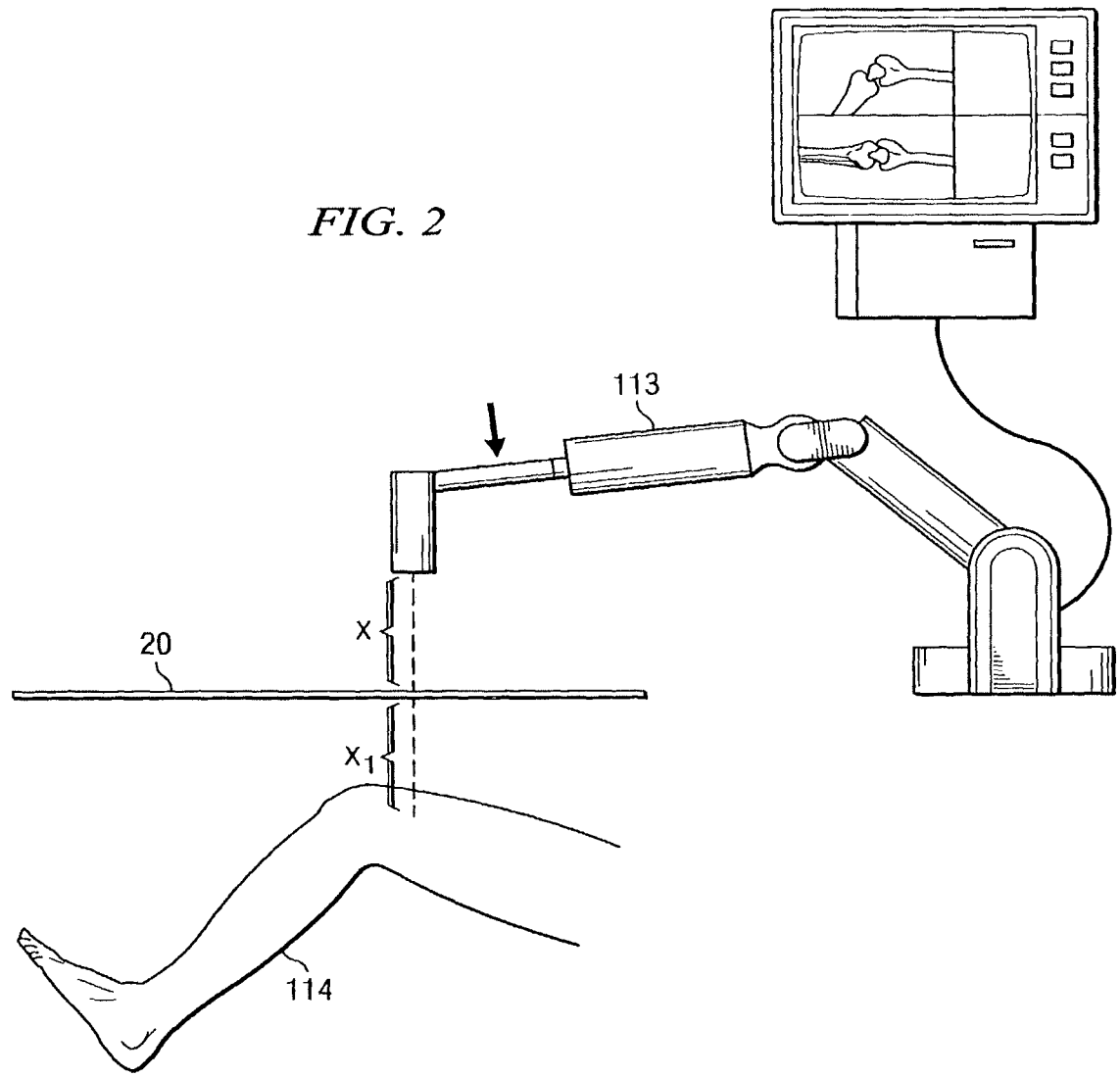
FIG. 2 illustrates an exemplary haptic device being used in conjunction with a computer-assisted surgery system.

Referring to FIG. 2, representative "haptic object" 20 is a two-dimensional virtual plane. However, it is only an example of haptic objects generally, which may be zero (e.g. a point), one (e.g. a virtual line or path), two (e.g. a virtual plane or flat surface), or three dimensional (e.g. a virtual curved surface, a cube or other solid object), and may have simple or complex geometric shapes. Haptic object 20 is preferably defined with respect to the space of a physical object, such as patient anatomy 114. Haptic object 20 is defined to guide and/or constrain the movement of haptic device 113. The distance between haptic device 113 and haptic object 20 is shown in FIG. 2 by X and the distance between patient's anatomy 114 and haptic object 20 is shown by $X_1$. Haptic object 20 may be used in connection with generating force feedback on haptic device 113. The generation of force feedback may also depend on various factors, for example, the velocity at which haptic device 113 is approaching patient's anatomy 114, the position of haptic device 113, haptic object 20, and/or the like. An algorithm which computes the current position of haptic device 113 relative to haptic object 20 may be used to provide information to the surgeon about the location of haptic device 113 relative to haptic object 20. When haptic device 113 comes within a predefined distance of haptic object 20, a stiffness parameter may be changed to make it more difficult to move haptic device 113. If desired, force may be applied in a direction away from anatomy 114 to resist the movement of haptic device 113 toward anatomy 114 or to move haptic device 113 away from anatomy 114.

It may not be appropriate to implement rigid haptic objects, such as virtual surfaces and walls, in certain cases. A surgeon will lose the ability to feel the anatomy in any direction that is rigidly constrained by the haptic device. In many applications, precise localization of anatomical features cannot be achieved by simply combining diagnostic datasets with a tool tracking system or precision robotic devices. Changes in the anatomy after the diagnostic datasets are taken, unsensed motion in the kinematic chain connecting the anatomical features of interest and the tracking system's camera or haptic device, registration errors, and inaccuracies in the localization devices will contribute to positioning errors. Although CAS systems may be used to position the surgical tool very close to the target region, more accurate positioning is often difficult or prohibitively costly. In some medical procedures, such as pedicle screw placement in the upper thoracic and cervical portions of the spine, deep brain neurosurgical procedures, etc., a slight inaccuracy may adversely affect the medical procedure being performed. Therefore, it is desirable in these types of procedures that a surgeon retain an ability to feel the anatomy.

Haptic devices can be used for registering patients to CAS systems and diagnostic data sets of the patient's anatomy, for example, by attaching a probe and touching it to a few selected anatomical landmarks, implanted fiducials, or multiple points on a surface of interest. They can be used for haptic exploration of diagnostic datasets to augment the visual display of this information. This exploration may occur intra-operatively while registered to the actual patient anatomy or pre-operatively in a purely virtual way. This haptic exploration is especially useful for exploring complex three-dimensional structures, where the surgeon's highly developed sense of touch can be used to explore complexities or subtleties of the dataset that may be difficult or impossible to display adequately on a two-dimensional or even three-dimensional visual display.

While performing traditional freehand surgery, surgeons rely on local anatomical features to ensure proper positioning of the surgical tool. If the ability of the surgeon to feel the patient anatomy is preserved, the surgeon can explore the local anatomy and correct these localization errors based on his expert knowledge of structures of interest. In this way, the final positioning is determined by nearby anatomical features rather than a tracking system sitting across the operating room or a robot whose base may not be rigidly connected to the patient.

A portion of surgical tool 112 coupled with a haptic device, for example the tip of surgical tool 112, may be used to sense properties of the local anatomy. The properties of the local anatomy may be used to position surgical tool 112 or to verify the proper positioning of surgical tool 112. The properties that may be sensed or monitored by the tool include electrical properties of the anatomy, force, pressure, stiffness, conductivity, etc. The information from the tip may be provided back to CAS system 11. The information may then, if desired, be correlated with information from diagnostic image datasets of the patient. If desired, information from the tool may be used to augment or replace the information from the image datasets. In either case the information may be used for better placement of surgical tool 112.

Location or position information of the tool may be sensed and provided back to CAS system 11 without the use of a separate sensor. The surgeon may manually move surgical tool 112 to the desired position. Position information of the tip of surgical tool 112 in the desired position may be determined directly by CAS system 11 and/or computer 10 without the use of a separate sensor. Other properties of the anatomy may be sensed by placing sensors at the tip of surgical tool 112. The output from the sensors may be provided back to CAS system 11 for processing.

The collected information may be used for a variety of purposes, such as alerting the user to registration errors, fully or partially correcting registration errors, displaying graphical representations of the information on display device 30, defining haptic objects to assist the user, displaying graphical representations of the information on display device 30 superimposed over one or more images of the anatomy, and/or the like. If desired, the collected information may be logged for use in machine learning techniques.

The combination of a haptic device and a CAS system is also useful for combining haptic exploration of diagnostic datasets and use of the haptic device as a primary input device for planning. In this way, haptic exploration naturally leads the user to a suitable plan for performing a procedure. Additionally, in some circumstances it is possible to have the haptic device and the tool coupled with it in the correct position for performing a procedure as a result of this exploration/planning process, eliminating the need to move the haptic device into position as a separate step.

Figure 3A:
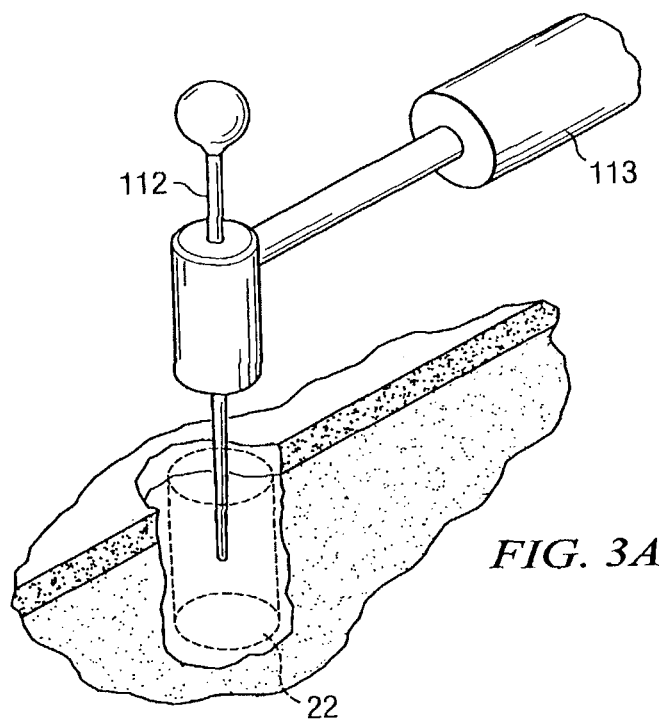
FIGS. 3A and 3B illustrate different types of haptic objects.

Referring to FIG. 3A, it may be desirable in certain procedures to confine the surgical instrument to a small working volume, in which case it may stay within a working area inside a haptic object during the entire procedure. It may be necessary in certain cases to segment or define manually certain important features, but for most applications automated segmentation of the diagnostic datasets will be sufficient for providing appropriate haptic feedback.

Figure 3B:
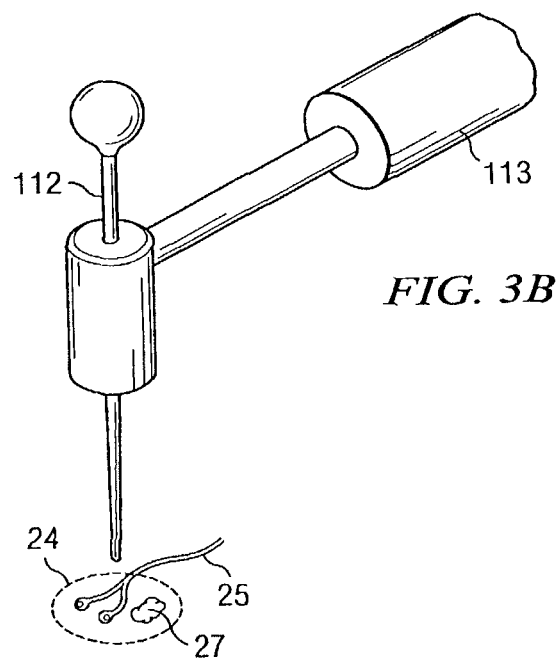

In the illustrated embodiment, one or more attractive haptic objects are associated with a target region for performing the surgical procedure and one or more repulsive haptic objects are associated with anatomical features to be avoided during the surgical procedure. For example, as shown in FIG. 3A, haptic object 22 defines a working area or volume for constraining movement of surgical tool 112. On the other hand, as shown in FIG. 3B, haptic object 24 defines a working area or volume for constraining movement of surgical tool 112 so that it is prevented from coming close to critical regions, such as nerves 25, organs 27, etc. For example, once the haptic objects are defined, the user performs surgical planning by pushing haptic device 113 around until a pose is found where the cues from the attractive haptic objects are active indicating that surgical tool 112, when attached to haptic device 113, would reach the target region, and where the cues from the repulsive haptic objects are inactive, indicating that surgical tool 112 would not penetrate any of the defined sensitive anatomical regions. In most cases, these requirements will not fully constrain the pose of the arm and the user can move the arm within this range of acceptable approaches based on any secondary criteria a user finds appropriate. In some cases, the arm may achieve an equilibrium state where multiple attractive or repulsive haptic cues act in opposite directions. The user might mistake this configuration to be an acceptable pose, even though the target region might not be reached or the critical anatomy regions might be violated. The user may be alerted to this situation in a number of ways, including audible or visual indicators, or by a haptic cue such as a vibration of haptic device 113. The user could then correct this situation by pushing the haptic device away from this pose. Once in a pose satisfactory to the user, haptic device 113 can be locked into position, using hardware brakes, control servoing techniques, or any other appropriate method to provide a stable physical reference for the surgical procedure.

If fine adjustments are desired, the haptic device can be operated using a mode where motion scaling, constraints, or other methods are used to make such corrections that might otherwise be beyond the dexterity of the surgeon. For example, a control servo can be enabled to lock the device to a certain finite stiffness at the approximate desired pose. The surgeon can then make fine adjustments to this pose using a variety of methods. For example, the surgeon may use a touch screen, a keyboard, a mouse, a trackball or voice inputs. If desired, the surgeon may push the end of the haptic device in the desired direction. In response to these inputs, the system would adjust the desired pose appropriately, possibly in small increments that would be difficult to achieve by direct positioning of the haptic device. It may be desirable to lock only a portion of the pose so that the surgeon can focus on a more limited number of adjustments at one time. This fine adjustment may occur after the coarse haptic positioning is complete, simultaneous with the coarse haptic positioning, or interleaved with the coarse haptic positioning.

For example, selecting a trajectory for a cranial neurosurgical procedure such as a biopsy, tumor resection, or deep-brain stimulation is a complicated 3-D planning problem. The surgeon must find a path to a target area while avoiding blood vessels and sensitive areas of the brain. If these regions can be turned into repulsive haptic objects, planning such a procedure may be as simple as applying a haptic constraint that keeps the trajectory of a tool guide passing through the target of interest, and allowing the user to pivot the device about this point until it settles into a suitable pose where none of the repulsive haptic objects are violated.

Figure 3C:
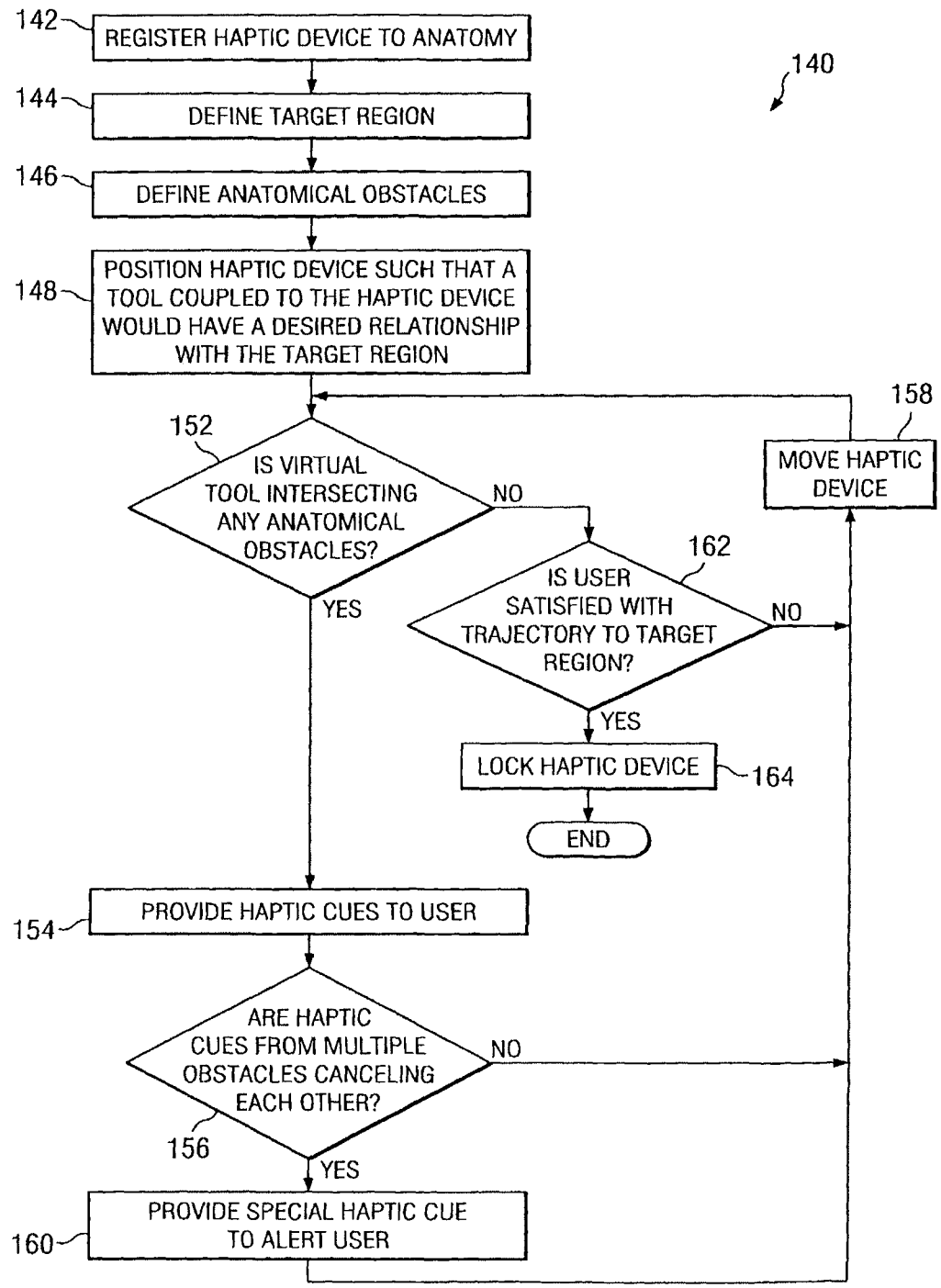
FIG. 3C is a flowchart of an exemplary method for intra-operative haptic planning of a surgical procedure.

FIG. 3C is a flowchart of an exemplary method 140 for intra-operative haptic planning of a surgical procedure. Haptic device 113 is placed in the operating room such that surgical tool 112 may be positioned over a large portion of a clinically reasonable range of surgical approaches for a given surgical procedure. Surgical planning using method 140 is performed in the presence of the patient and preferably without surgical tool 112 being coupled to haptic device 113. Surgical tool 112 may be a non-contact medical device, such as a diagnostic or therapeutic radiation source. If desired, surgical planning using method 140 may be performed with surgical tool 112 coupled to haptic device 113 but being in a retracted state. When surgical tool 112 comprises a non-contact medical device, it is preferably in a disabled state. A representation of the anatomy of the patient to be operated on may be displayed on display device 30 along with a "virtual tool". The virtual tool may be a high-fidelity representation or a schematic representation of surgical tool 112, such as an axis, a point, or other feature of surgical tool 112. The virtual tool indicates relative to the anatomy of the patient, the position and/or angle of surgical tool 112 or some portion thereof if the surgical tool had been coupled to haptic device 113 in its normal or enabled state.

In step 142, haptic device 113 is registered to the anatomy of the patient. If desired, the representation of the anatomy of the patient displayed on display device 30 may also be registered with the anatomy of the patient so that information in diagnostic or planning datasets may be correlated to locations in the physical space. Any method for registering, now known or later developed, may be used. In step 144, the target region is defined. The target region may be, for example, a tumor, an osteophyte, an anatomical target for deep-brain stimulation, a bone channel, and/or the like. The target region may be defined in any manner now known or later developed. For example, the user, such as the surgeon, may manually identify the target region on display device 30. If desired, the surgeon may define the target region by touching one or more points on the target region or circling the target region on display device 30 with a tool. Alternatively, the surgeon may define the target region by pointing a tool mounting axis of haptic device 113 to the target region or by using haptic device 113 as an input device. Preferably, the identified target region is automatically highlighted on display device 30. The tool mounting axis of haptic device 113 may be of any shape, for example curved, straight, and/or the like. Regardless of the manner in which the target region is defined, it is desirable that once defined, the target region be clearly displayed on display device 30 for confirmation. One or more attractive haptic objects, such as haptic object 22 of FIG. 3A, may be associated with the target region.

In step 146, anatomical obstacles to be avoided are defined. The anatomical obstacles comprise features to be avoided during surgery, such as major blood vessels, tendons, nerves, critical areas of the brain, organs, healthy bones or other tissues, and/or the like. The anatomical obstacles may be defined in any manner now known or later developed. For example, the surgeon may manually identify the anatomical obstacles on display device 30. If desired, the surgeon may define the anatomical obstacles by touching one or more points on the anatomical obstacles or circling the anatomical obstacles on display device 30 with a tool. Alternatively, the surgeon may define the anatomical obstacles by pointing the tool mounting axis of haptic device 113 to the anatomical obstacles or by using haptic device 113 as an input device. Preferably, the identified anatomical obstacles are highlighted on display device 30. Regardless of the manner in which the anatomical obstacles are defined, it is desirable that, once defined, the anatomical obstacles are clearly displayed on display device 30 for confirmation. One or more repulsive haptic objects, such as haptic object 24 of FIG. 3B, may be associated with the defined anatomical obstacles. Preferably, each anatomical obstacle has one repulsive haptic object associated with it, although if desired more than one repulsive haptic object may be associated with an anatomical obstacle.

In step 148, haptic device 113 is positioned, preferably by the surgeon, such that if surgical tool 112 were coupled to haptic device 113 or if surgical tool 112 were in an operating state, then the appropriate portion of the surgical tool would have the desired relationship with the target region. For example, when coupled to haptic device 113, surgical tool 112 would penetrate the target region. Surgical tool 112 is in its operating state when it is coupled to haptic device 113 and is not retracted and/or is not disabled. Step 148 is preferably performed without regard to whether or not the tool may intersect the anatomical obstacles in this position. A virtual tool displayed on display device 30 is such that it's position and orientation corresponds to the position and orientation of surgical tool 112 if surgical tool 112 had been mounted on haptic device 113 or if surgical tool 112 were in its normal operating state. Thus, the surgeon may position haptic device 113 in the desired pose while viewing the display on device 30, such that the virtual tool has the appropriate relation with the target region.

In step 152, a determination is made as to whether the virtual tool is intersecting any anatomical obstacles. If the virtual tool is not intersecting any anatomical obstacles, then the process starting at step 162 is executed. Otherwise, the process starting at step 154 is executed. In step 154, haptic cues are provided by haptic device 113 to the user. The haptic cues may be provided to the user based on one or more haptic objects, for example the attractive haptic object(s) associated with the target region and/or the repulsive haptic object(s) associated with the anatomical obstacles. The repulsive haptic object(s) generate forces and/or torques that guide haptic device 113 away from poses where the virtual tool would intersect the anatomical obstacles. Preferably, the repulsive haptic cues are active when the virtual tool penetrates the repulsive haptic objects or is in proximity to the repulsive haptic objects. The attractive haptic object(s) cause the haptic device to generate forces and/or torques that guide haptic device 113 toward poses where the virtual tool has the desired relationship with the target region.

It is possible that the position of haptic device 113 may be such that cues from multiple haptic objects cancel each other out even though the virtual tool may be violating the anatomical obstacles. As such, in step 156, a determination is made as to whether haptic cues from multiple obstacles are canceling each other out. If haptic cues from multiple obstacles are not canceling each other out, then the process starting at step 158 may be executed. If haptic cues from multiple obstacles are canceling each other out, then in step 160, a special haptic cue, for example a vibration, may be provided to alert the user of this situation and the process starting at step 158 may be executed.

In step 158, haptic device 113 is moved, preferably by the surgeon. Haptic device 113 is preferably moved based at least in part on the haptic cues provided by haptic device 113 to the surgeon. The position of surgical tool 112 had it been coupled to haptic device 113 is tracked by the virtual tool and displayed on display device 30. Preferably, the user moves haptic device 113 until an equilibrium pose is found. In the equilibrium position, the cues created by the attractive haptic objects are active and those created by the repulsive haptic objects are inactive. The process starting at step 152 may then be executed to determine whether the virtual tool is intersecting any anatomical obstacles.

In step 162, a determination is made as to whether the user is satisfied with the trajectory to the target region. The user may make this determination by viewing the virtual tool relative to the target region as illustrated on display device 30. If the user is not satisfied with the position and/or the orientation of the virtual tool, then the process starting at step 158 may be executed. If the user is satisfied with the position and the orientation of the virtual tool relative to the target region and the obstacles, then the process starting at step 164 may be executed. The user may indicate its satisfaction in one or more of a number of ways. For example, the user may issue a voice command to indicate that it is satisfied with the position and orientation of the virtual tool. If desired, the user may activate a foot pedal or a button associated with the computer-assisted surgery system or haptic device 113 to indicate its satisfaction. If desired, the user may indicate its satisfaction via a touch screen, a keyboard, a mouse, and/or the like, associated with the computer-assisted surgery system or haptic device 113. In step 164, haptic device 113 may be locked in the current pose.

Once the pose of haptic device 113 is locked, the surgical procedure may be performed, for example by coupling surgical tool 112 to haptic device 113 or by placing surgical tool 112 in its fully functional or operational configuration. Because the pose of surgical tool 112 relative to the anatomy has already been determined with the aid of the virtual tool, surgical tool 112 will achieve the desired position when it is coupled to haptic device 113 or when it is configured for use.

The illustrated method for intra-operative haptic planning of a surgical procedure may be implemented in software, hardware, or a combination of both software and hardware. The steps discussed herein need not be performed in the stated order. Several of the steps could be performed concurrently with each other. Furthermore, if desired, one or more of the above described steps may be optional or may be combined without departing from the scope of the present invention. Furthermore, one or more of the above described steps may be performed outside the operating room to save time spent in the operating room. For example, steps 144 and 146 may be performed prior to bringing the patient into the operating room and prior to step 142.

A technical advantage of this exemplary embodiment for intra-operative haptic planning of a surgical procedure is that it provides for tighter coupling of the planning and execution phases of the surgical procedure. Planning for the surgical procedure is preferably performed intra-operatively with respect to the patient. Thus, when planning is complete, the haptic device is in position for executing the surgical plan. No additional motion of the haptic device is required to initiate the execution phase. Furthermore, by using a virtual tool to determine the trajectory of the real surgical tool to the target region, injury to anatomical features may be avoided during the planning phase.

Figure 4A:
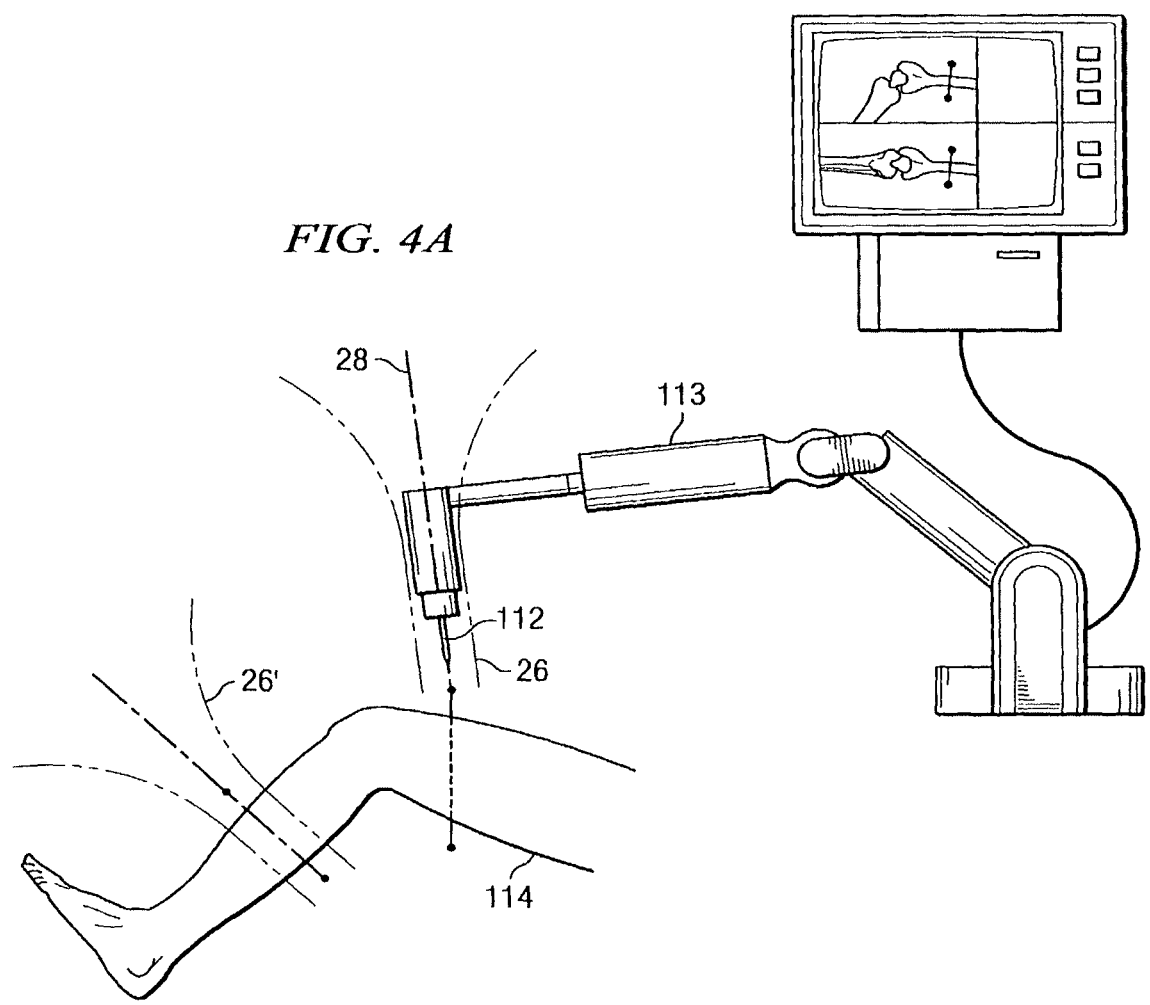
FIG. 4A illustrates the use of a dynamic haptic object for placement of a haptic device.

A haptic object may be of any shape or size. As shown in FIG. 4A, haptic object 26 may be funnel shaped to guide a medical device, for example a surgical tool, coupled to haptic device 113 toward a target area on anatomy 114 of the patient. The path of the haptic object may depend on a surgical plan. An algorithm may be used to create the funnel shaped haptic object illustrated in FIG. 4A. The information desired to create the funnel shaped haptic object may be based on a surgical plan. If desired, haptic object 26 may move with haptic device 113. This allows guidance of the surgical tool toward the target area from the current position of haptic device 113. Thus, the surgical tool may be guided toward the target area from any position in proximity to anatomy 114. Furthermore, the surgical tool may be guided from a current pose to a desired pose.

Haptic object 26 may be of any shape, for example, a line, a curve, a cylinder, a funnel, and/or the like. Haptic object 26 is, in the illustrated example, defined as a virtual pathway to facilitate interactive positioning of haptic device 113 and/or surgical tool 112 coupled to haptic device 113 at a desired position. Haptic object 26 guides surgical tool 112 coupled to haptic device 113 from an initial position and/or pose toward a target area and/or a desired pose relative to anatomy 114 of the patient. If desired, haptic object 26 may guide surgical tool 112 to the target area along a path or trajectory 28. The path or trajectory 28 from the initial position to the target area may depend on the surgical plan. The path may be of any shape, for example a straight line, a curve, a funnel, a cylinder, and/or the like. Based at least in part on haptic object 26, haptic forces are applied to haptic device 113 as the user moves the surgical tool or haptic device to guide the user in moving the surgical tool 112 along path 28 toward the target area.

Haptic object 26 is preferably steerable or reconfigurable. For example, the haptic object may be defined to move or to change position and/or orientation as the haptic device (or the surgical tool or instrument coupled to it) moves. This allows, for example, the user to guide surgical tool 112 toward the target area from almost any position in proximity to anatomy 114. This reconfigurability or steerability of haptic object 26 also allows the user to guide surgical tool 112 to the desired pose from its current position and/or pose.

Haptic object 26 may also be allowed to move from a pre-defined path or position in order to avoid obstacles, preferably without deviating from the target area. This is especially useful in avoiding obstacles in the path of haptic device 113 that computer-assisted surgery system 11 may not be aware of. Thus, surgical tool 112 may be steered by the user toward the target area without colliding with other surgical tools and equipment, the patient, or operating room staff.

Steering, moving or reconfiguring is, in a preferred embodiment, in response to application of a force or torque on the haptic device or the haptic object that exceeds a threshold value. For example, if the user pushes haptic device 113 against the haptic object with a force that exceeds a threshold, then the haptic object will be repositioned, reconfigured or modified to a new configuration based on the input force or torque. Preferably, haptic object 26 moves in the direction of the force or torque thereby providing an intuitive method for repositioning or realigning haptic object 26.

If desired, haptic object 26 may move to a new location if the target area is changed. Thus, as shown in FIG. 4A, haptic object 26 may be moved from an initial position to a new position, as shown by haptic object 26', in response to a change in the target area.

In an alternative embodiment, haptic object 26 may be defined as virtual linear or non-linear springs, dampers, clutches, and/or the like, logically applied to one or more joints of haptic device 113. One or more joints of haptic device 113 may comprise virtual detents corresponding to the final desired pose of haptic device 113. Preferably, standard joint-space control techniques are used to implement the haptic objects at each joint and conventional inverse kinematics techniques are used to determine the joint positions corresponding to the desired Cartesian position/angle of the haptic device. The user may avoid obstacles by specifying the sequence in which the joints of haptic device 113 "lock" into their detents. The user may be permitted to modify the selected sequence by "unlocking" joints during positioning of surgical tool 112, especially if the sequence is determined through a trial-and-error technique. Interactive unlocking of a joint by the user may be based on the magnitude, duration or dynamic property of the force and/or the torque at that joint by the user. A graphical user interface, a footswitch, a keyboard, a button, and/or the like, communicatively coupled to haptic device 113 may be used to unlock a joint. If desired, once the desired pose is achieved, the ability to unlock the joints may be disabled to prevent inadvertent motion of haptic device 113.

In another alternative embodiment, haptic object 26 may be defined by virtual linear or non-linear springs, dampers, clutches, and/or the like, logically associated with one or more redundant degrees-of-freedom of haptic device 113. For example, if a haptic device comprising of four joints is used to position the tip of surgical tool 112, then the haptic device 113 may be moved along one of the degrees-of-freedom without affecting the position of the tip. Haptic object 26 may be associated with the redundant degree-of-freedom to permit the user to interactively modify the position of haptic device 113.

Figure 4B:
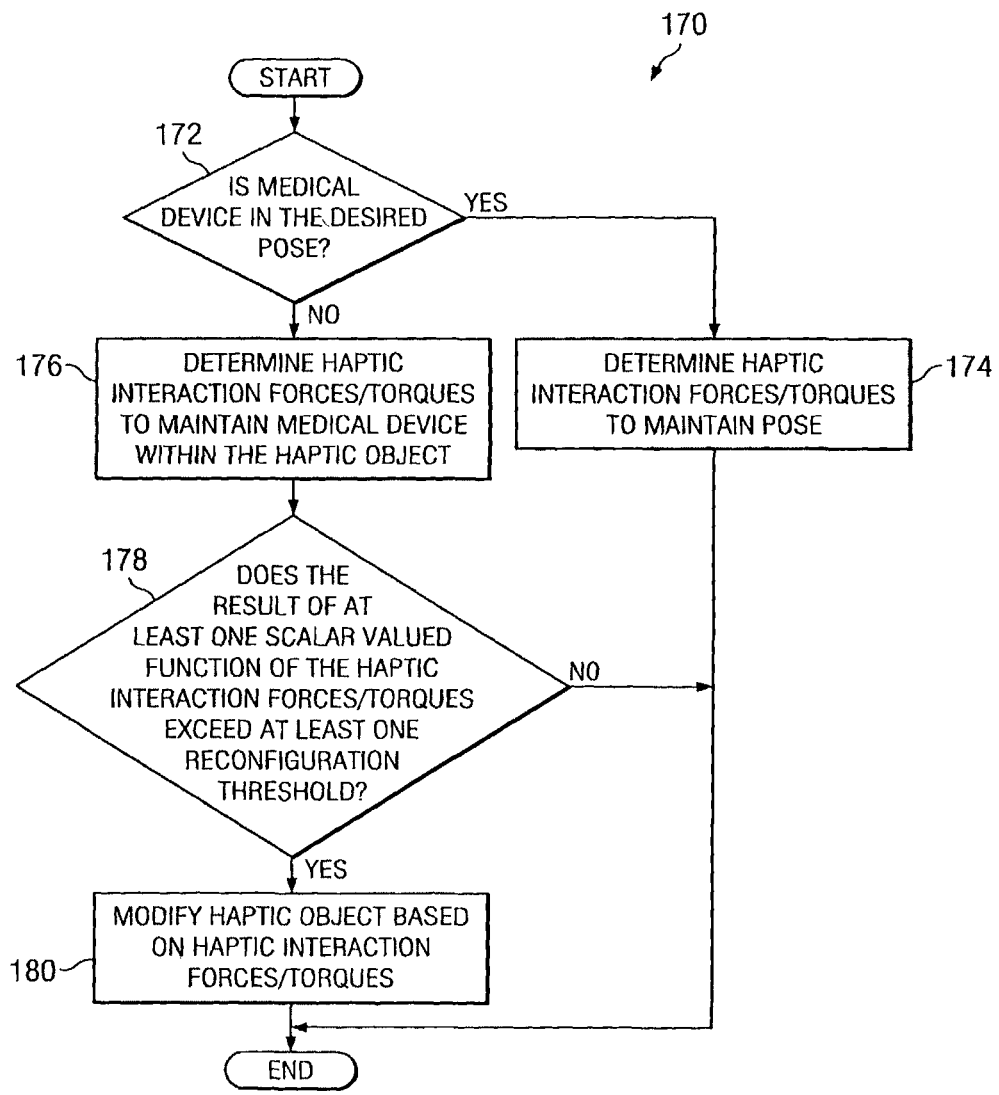
FIG. 4B is a flowchart of a method for interactive haptic positioning of a medical device coupled to a haptic device.

FIG. 4B is a flowchart of a method 170 for interactive haptic positioning of a medical device, for example surgical tool 112 mounted to haptic device 113, using a reconfigurable or steerable haptic object 26, all as shown in FIG. 4A. If desired, the reconfigurability of the haptic object may be user-configurable such that the user may turn this feature ON or OFF depending on the application or depending on the step of a particular application. When the reconfiguration feature is enabled, method 170 is preferably executed periodically.

In step 172, a determination is made as to whether the medical device is in a desired pose. This determination may be made by using sensing information from one or more position sensors, such as encoders or resolvers, which may be integrated in the haptic device. If desired, this determination may be made by using sensing information from an external device, such as a laser interferometer, a camera, and/or other tracking device.

If in step 172, it is determined that the medical device is in the desired pose, then in step 174, haptic interaction forces and/or torques to maintain the pose of the medical device are determined. This determination may be made based at least in part on the position and/or velocity of the haptic device and/or the medical device relative to the desired pose. Any control algorithm now known or later developed may be used for this determination, for example, robust control, adaptive control, hybrid position/force control, Proportional-Derivative (PD) control, Proportional-integral-Derivative (PID) control, Cartesian based control, inverse Jacobian control, transpose Jacobian control, and/or the like. The determined haptic interaction forces and/or torques may be transformed and provided to the haptic device. If in step 172, it is determined that the medical device is not in the desired pose, then in step 176, haptic interaction forces and/or torques to maintain the medical device within a haptic object are determined so that the medical device may be guided toward the target area. In step 178, a determination is made as to whether the result of at least one scalar valued function of the haptic interaction forces and/or torques calculated in step 176 exceeds at least one reconfiguration threshold. The reconfiguration threshold may be user-configurable. A scalar valued function computes a value based on one or more input values. In an exemplary embodiment, the scalar valued function may be the square root of the sum of the squares of the input values. A scalar valued function may be applied to one or more haptic interaction forces to provide a scalar value. The resulting scalar value may be compared to the reconfiguration threshold. Dynamic properties of the haptic interaction forces and/or torques, such as direction, duration, and/or the like, may also be considered.

If the result of none of the scalar valued functions exceeds the reconfiguration threshold, then the process ends. Otherwise in step 180, haptic object 26 is modified based at least in part on the haptic interaction forces and/or torques. For example, if the surgeon guides the haptic device such that the haptic device in effect pushes against the haptic object, the value of the scalar valued function of the haptic interaction forces and/or torques generated to keep the haptic device within the haptic object may exceed the reconfiguration threshold. In such a case, it is desirable that the haptic object be modified, for example in the direction of the force applied by the surgeon such that the surgical tool is maintained within the haptic object. The modification of the haptic object may comprise changing the size of the haptic object, changing the shape of the haptic object, pivoting the haptic object along the target area of the patient's anatomy, and/or the like.

A technical advantage of this exemplary embodiment for interactive haptic positioning of a medical device is that by modifying a haptic object based on the haptic interaction forces and/or torques, greater flexibility is provided to the surgeon. Thus, the surgeon may approach the target area without colliding with other surgical tools and equipment, the patient or operating room staff, and still be provided with haptic cues to enable the surgeon to guide the surgical tool to the target area.

The illustrated method for interactive positioning of a haptic device using a reconfigurable (repositionable, steerable) haptic object may be used in any situation where it is desirable to move the haptic device, optionally coupling a component of interest, such as a medical device, for example a surgical tool, and/or the like, within a cluttered or safety-critical environment. If desired, the haptic device itself may be the component of interest. The illustrated method may be used in a variety of applications, such as a procedure where virtual constraints and/or haptic cues are used to move the component of interest into a predefined location and/or orientation and safety or other concerns make autonomous device motions undesirable. For example, the method may be used in an implant placement procedure, a biopsy procedure, deposition of therapeutic implants, diagnostic palpation of internal or external anatomy, tumor removal, radiation therapy, artistic or commercial sculpting, artistic or commercial painting, scientific or engineering experiments, such as surface digitizing, sample collection, circuit board probing, manual assembly, fabrication or testing of mechanical and/or electronic components or assemblies, material handling, and/or the like.

For rehabilitation and/or physical therapy applications, a haptic device may be coupled to the patient using an orthotic device, which may require the patient to grasp a handle. In such an embodiment, the haptic device may be coupled to a computer system having a user console. The computer system may or may not be a CAS system, but may be a computer system designed for rehabilitative or physical therapy applications. If desired, the computer system may be integrated with computer 10. The orthotic device may have straps, braces, shells, or cast features to provide a firm or loose connection as desired. The orthotic device allows the haptic device to guide, monitor, and/or assist rehabilitative motions or other exercises. For example, the patient or a therapist may couple the patient's arm or leg to the haptic device and lead it through a desired motion while the haptic device records the properties of the motion. The motion can then be repeated multiple times without the assistance of the therapist. The haptic device may also be used to monitor the patient's efforts to move by noticing how much effort is required to move the patient, or through the use of force sensing devices which may be coupled to the haptic device at or near the location where the patient interfaces with the haptic device. The haptic device may also be used to simply constrain the patient's motion to the defined path which requires the patient to advance along the defined path using their own strength. Modes where there is a shared effort between the patient and the haptic device may also be advantageous. It is desirable that when used in this manner, the haptic device operate in a safe manner because it is so close to the patient, who may have only partial function in one or more extremities. It may be undesirable for the haptic device to move to new positions automatically or autonomously. However, it may be desirable to reposition the haptic device, for example to permit initial attachment to or grasping by the patient, so that the haptic device may be moved to different starting positions between different exercises or repetitions of the same exercise, or in the course of performing the rehabilitative motions or exercises. A physical therapist may provide the interactive input for repositioning the haptic device. If desired, the patient may provide such input while interfacing with the haptic device.

The illustrated method for interactive haptic positioning of a surgical tool using a reconfigurable or steerable haptic object may be implemented in software, hardware, or a combination of both software and hardware. The steps discussed herein need not be performed in the stated order. Several of the steps could be performed concurrently with each other. Furthermore, if desired, one or more of the above described steps may be optional or may be combined without departing from the scope of the present invention.

Figure 5:
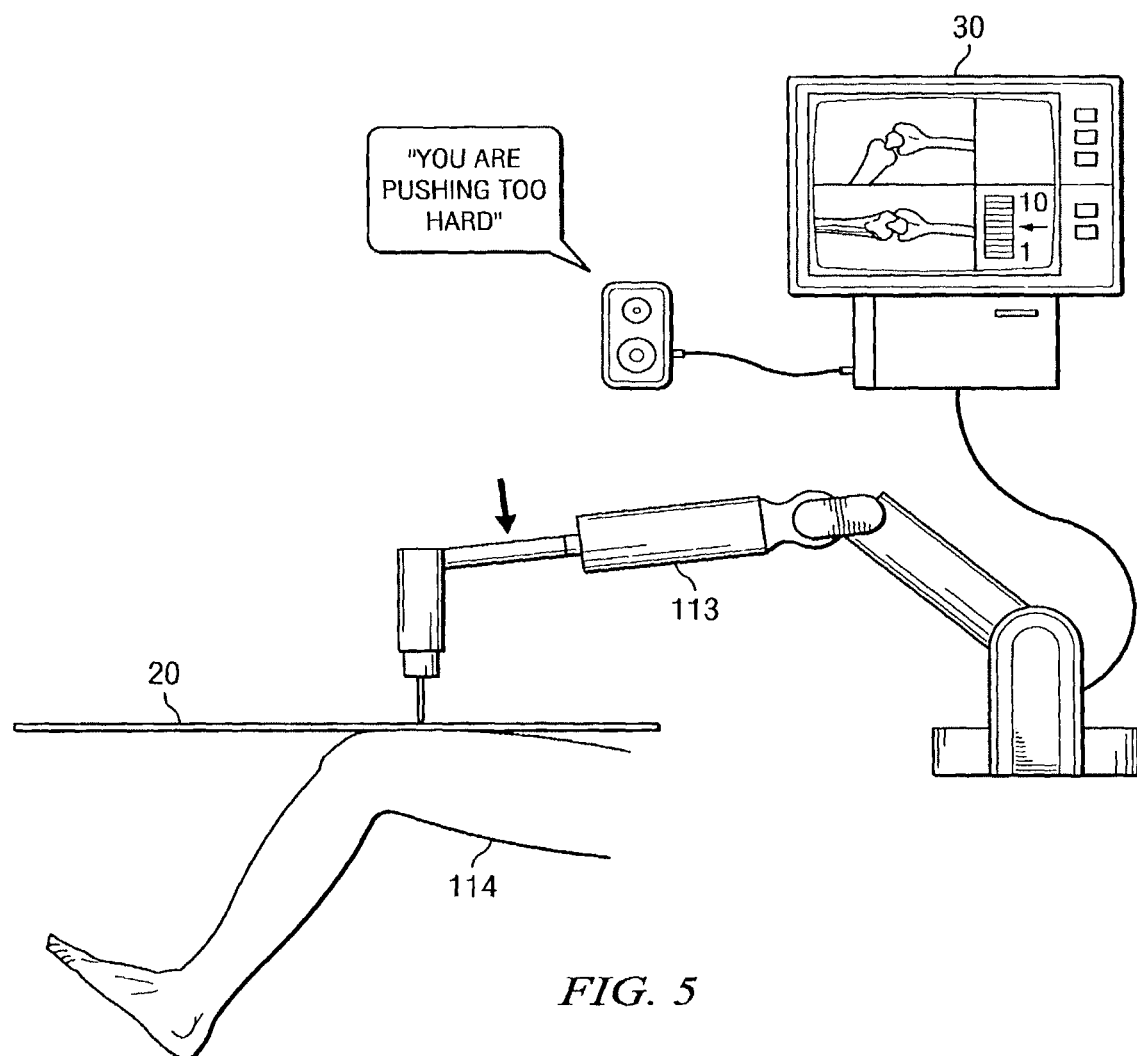
FIG. 5 illustrates the use of an exemplary haptic device in conjunction with a computer-assisted surgery system.

Referring now to FIG. 5, when the user interacts with a haptic object, such as haptic object 20, it is sometimes desirable to know the magnitude of forces applied to the haptic object or the amount that a real or virtual tool or implant is penetrating the haptic object. For non-trivial haptic objects, or those with complicated two or three dimensional forms, it may be difficult to present this information in a manner that is simple for the user to understand. However, the desirable piece of information is often the local penetration distance or haptic repulsion force. While these can be up to three-dimensional vector quantities, the magnitude (or length) of such vectors, possibly in the direction of a local unit normal of the haptic object, are most useful for augmenting the haptic interaction of the user. These magnitudes are simple one-dimensional quantities and can be conveyed to the user in a variety of methods, including meters, dials, numerical displays, graphs, and other visual methods, but also with audio, tactile, haptic, or other means.

Though a complete message is conveyed directly by haptic device 113 to the hand of the surgeon, a visual or audible display can be used to support rich interactions between the user and the system. For example, well known and commercially available speech recognition techniques can be used to provide a verbal method for the user to communicate information or instructions to the computer aided surgery system. Speech output from the computer aided surgery system 11 can also be used for communicating information to the user including status information, warning messages, event notification, and responses to user queries, whether communicated verbally or through some other method. Computer monitors, projection displays, wearable displays, head-mounted displays, stereoscopic views, holographic displays, and/or other visual display devices can be used to provide schematic anatomic representations, images of diagnostic datasets, instructions or guides for the surgical procedure, depictions of virtual and haptic objects, system status information, patient information, and other information that is easily communicated over a visual display. Any other input or output device could similarly be used to augment the haptic interaction between the user and the computer surgery system.

A visual and/or audio display of the penetration into a haptic object of a predetermined stiffness of a surgical device's depth, force and/or velocity is provided. The haptic object is based upon information from the computer-assisted surgical system. The display is one-dimensional in order to facilitate the communication of the local penetration magnitude of the surgical device into the haptic object.

During surgery, the haptic device may be used to enhance the performance of the surgeon in, for example, such tasks as holding a tool steady, making straight cuts, or moving a tool tip along a path or surface. The haptic device can replace mechanical cutting jigs and alignment apparatus used for aiding in the placement of and preparation of anatomy for implanted medical devices. Virtual haptic surfaces may be used to replace physical cutting blocks. The virtual haptic surfaces in this instance are preferably software entities that can be easily and cheaply created from the models of the implant. The virtual haptic surfaces can be created with curved shapes, which more closely match the underlying anatomy and enable implant designs that require less bone or tissue removal.

Sculpting of a physical object, such as a bone, frequently requires multiple planar features to be created in the bone and/or on the surface of the bone. A haptic object may be defined to assist in such sculpting. The shape of the defined haptic object may correspond substantially to the desired resulting shape of the physical object after sculpting. The physical object and the haptic object may have segments or surfaces with abrupt transitions and/or may have portions with short radius of curvature. As such, it is possible that a surgical tool coupled to the haptic device and being used to sculpt the physical object may abruptly fall off one segment causing unintentional damage to the physical object or other objects in the vicinity of the physical object, or be distracting or disturbing to the user. A segment may be one-dimensional, two-dimensional or three-dimensional.

In order to address this problem, haptic object is dynamically modified during sculpting in order to prevent the surgical tool or the haptic device from following an abrupt transition from one segment of the haptic object to another segment. Preferably, the haptic object remains in the modified form only so long as it is desirable to prevent abrupt transitioning of the surgical tool or the haptic device from one segment to another. Once the cutting or portion thereof is complete, the haptic object may be returned to its original configuration, for example to its original shape, size, orientation, and/or the like. The modification of the haptic object may comprise creating another haptic segment that prevents the surgical tool from following an abrupt transition from one segment of the haptic object to another segment of the haptic object, modifying an existing segment of the haptic object, for example by extending the existing segment beyond its boundary, and/or the like.

Figures 6A, 6B:
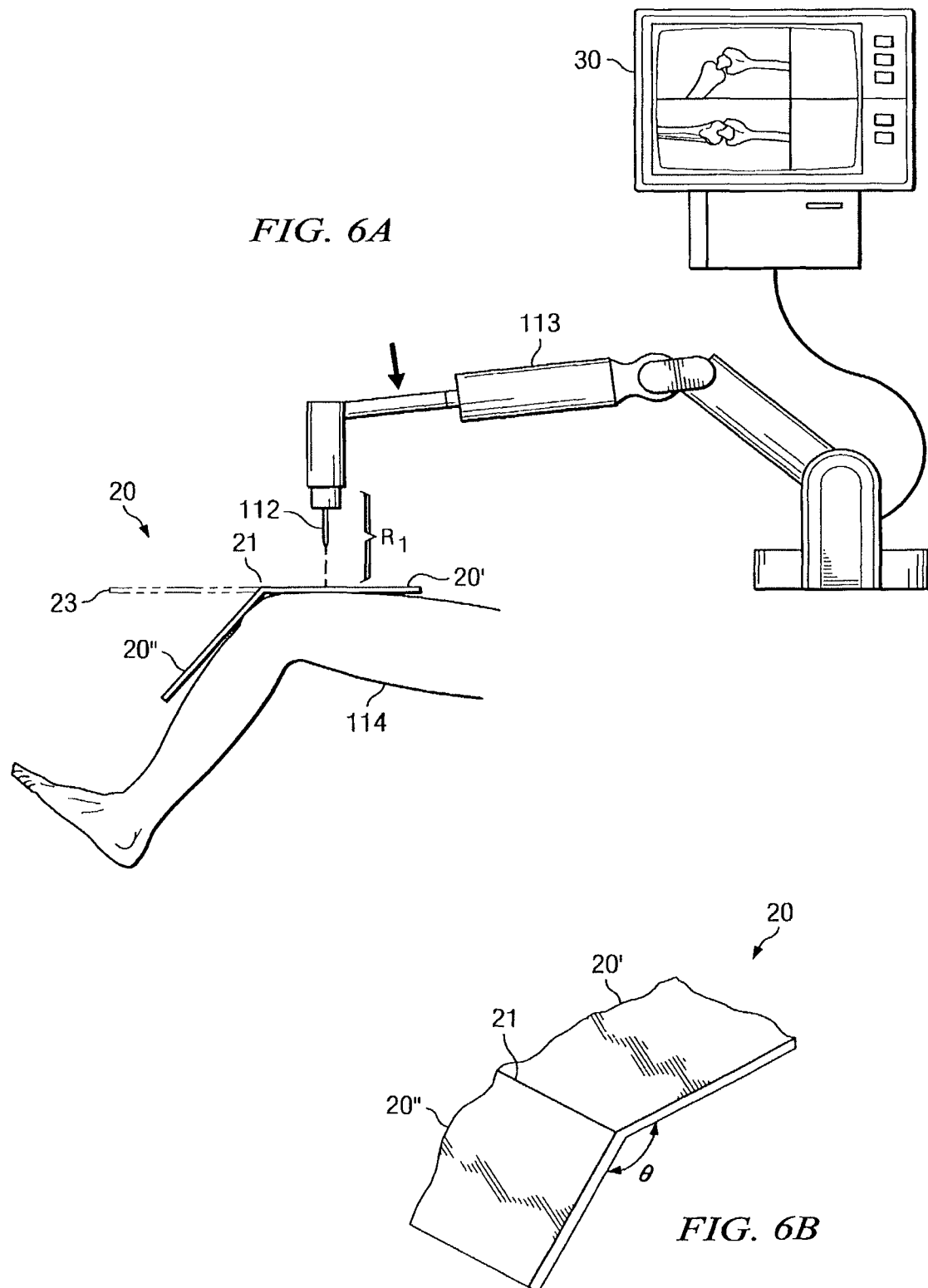
FIG. 6A illustrates an exemplary haptic device being used for haptic sculpting of physical objects.
FIG. 6B illustrates an exemplary haptic object for haptic sculpting of physical objects.

FIG. 6A illustrates an exemplary haptic device being used for haptic sculpting of physical objects with high curvature. FIG. 6B illustrates an exemplary haptic object 20 for haptic sculpting of physical objects with high curvature. Referring now to FIGS. 6A and 6B, in certain cases, the desired shape for an anatomical region to be prepared with the aid of a haptic object may include sharp external edges. It is difficult to properly execute cuts without slipping off these edges, resulting in rounding of the edges and other unwanted artifacts in the resulting contour of the anatomy. An improved method for preparing these types of shapes involves dynamically enabling and disabling portions of the haptic surface. In particular, this method is helpful if a haptic object contains at least one sharp external edge where the local angle between the two portions joined by the edge as depicted in FIGS. 6A and 6B is less than 180 degrees. The method includes a way of selecting one of these portions, which may include any of the user input modalities mentioned herein, but the preferred method is based on proximity to the haptic object. When one of the portions is selected, that portion of the haptic object is extended beyond the joining edge to provide a continuous guide surface. When the extension is no longer required, the user can return the haptic object to its original configuration by moving the haptic arm away from the portion or using any other input modality.

For example, in a total or unicompartmental knee replacement procedure, multiple planar cuts are often required to prepare the femur for the femoral implant. A haptic object is defined in software that contains portions closely related to the desired femoral cuts. In experiments, when the user attempts to resect the bone using a cutting burr mounted in the haptic arm using the full haptic object, it is difficult to make the straight cuts without slipping from one portion to another and frequently moving the burr beyond the desired region. This slipping may result in damage to tendons, blood vessels, ligaments, and other structures and distract the user. If instead, each cutting plane of the haptic object is extended when the user brings the cutting burr within close proximity to that portion, it is much easier to create straight cuts without moving beyond the local anatomical site. The portion is returned to its original extent by simply moving back away from it, at which time the user can bring the cutting burr into contact with any of the other portions to extend them in a similar manner. While foot pedals, voice commands, or other input modalities can be used to control the extension of each plane, controlling them in the preferred manner described previously requires no additional hardware and is extremely simple for the user. However, a visual display of the haptic object and the extended portion is also helpful for helping the user to understand more complex haptic objects, especially where their view of the cutting is limited due to obstructions or a minimally-invasive technique.

FIG. 6A shows an exemplary system for dynamically extending a haptic object. A representation of the physical object, for example the anatomy of the patient to be sculpted, may be displayed on display device 30. The representation of the physical object may comprise a two-dimensional or three-dimensional drawing or image. The image could be, for example, a two-dimensional medical diagnostic dataset or a three-dimensional medical diagnostic dataset of the patient. In FIG. 6A, haptic object 20 includes two different portions (20' and 20") divided by a well defined edge 21. When haptic device 113, the surgical tool, or the virtual surgical tool comes within a predefined distance, say Ri, of one portion, say portion 20', that portion of haptic object 20 is activated. If desired, the activated portion of the haptic object 20 may be extended as shown by the broken lines 23 in FIG. 6A. When haptic device 113 moves to within a predefined distance of another portion, say portion 20", the new portion of haptic object 20 may be activated. If desired, the newly activated portion of haptic object 20 may be extended.

It is desirable that haptic object 20 with high curvature be logically divided into or be approximated by a plurality of portions or segments without high curvature. For example, as shown in FIG. 6A, haptic object 20 may be logically divided into a plurality of portions 20' and 20" separated by an edge 21. Although, it is preferable to logically divide a haptic object into a plurality of segments, the haptic object itself may be defined using a logical combination of a plurality of segments. For example, a plurality of segments may be initially defined and the haptic object may be defined as a logical combination of one or more of the plurality of segments. If desired, the haptic object may comprise a regular or irregular arrangement of volume elements, or voxels, some or all of which may be labeled. It may be desirable to only label the voxels on the surface of the object in this manner.

Figure 6C:
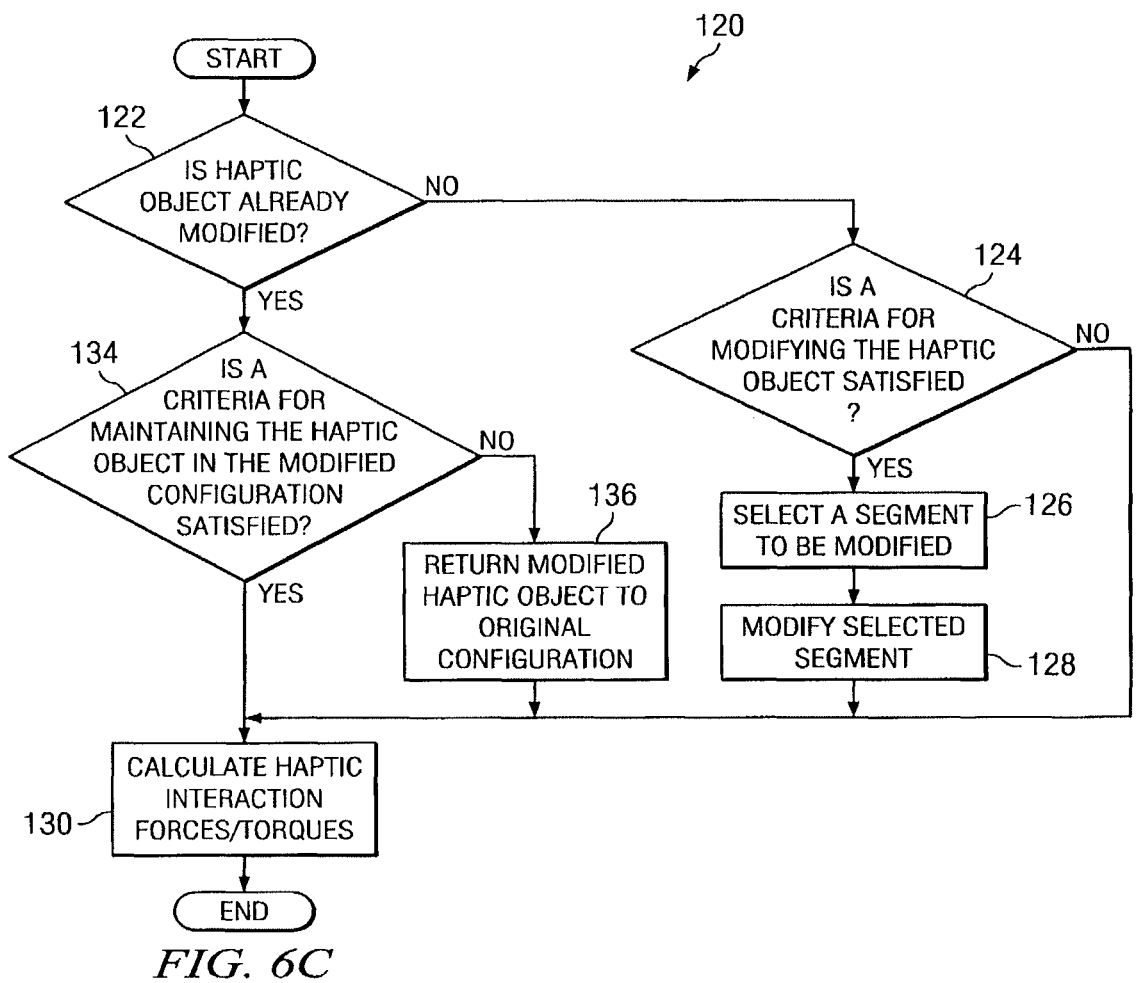
FIG. 6C is a flowchart of a method for dynamically modifying a haptic object.

FIG. 6C is a flowchart of a method 120 for dynamically modifying a haptic object, such as haptic object 20 of FIGS. 6A and 6B. If desired, the dynamic modification feature may be user-configurable such that the user may turn this feature ON or OFF depending on the application or depending on the step of a particular application. When the dynamic modification feature is enabled, method 120 is preferably executed periodically.

In step 122, a determination is made as to whether a configuration of the haptic object, say haptic object 20, has already been modified, for example by modifying a segment of the haptic object or by adding a new segment. In the preferred embodiment, the value of a configuration flag may be checked to determine if haptic object 20 has already been modified. If haptic object 20 has not already been modified, then in step 124, a determination is made as to whether one or more criteria for modifying the configuration of haptic object 20 is satisfied. The criteria may be proximity of surgical tool 112 coupled to haptic device 113 to haptic object 20, penetration of haptic object 20 by surgical tool 112, gestural motions of surgical tool 112, gestural or other motion of surgical tool 112 relative to the position of haptic object 20, a fixed or variable time period, detection of an unwanted slippage over edge 21, and/or the like. If desired, the criteria may be proximity of the representation of surgical tool 112 to haptic object 20, penetration of the boundaries of haptic object 20 by the representation of surgical tool 112, gestural or other motion of the representation of surgical tool 112 relative to the position of haptic object 20, and/or the like. When modification of the configuration of haptic object 20 comprises modifying a segment of haptic object 20, preferably the same criteria is used to determine if any of the segments should be modified. However, if desired, different segments may be modified based on different criteria. In such an embodiment, each of the plurality of segments may have one or more criteria associated with it.

If in step 124, it is determined that at least one criteria for modifying the configuration of haptic object 20 is satisfied, then in step 126, the segment to be modified is selected. Alternatively, a segment in proximity to which a new haptic segment is to be created may be selected in step 126. In an alternative embodiment, the process starting at step 126 may be executed if a predefined logical combination of a set of criteria are satisfied. Preferably, the segment that is closest to haptic device 113 is selected. However, if desired, other criteria may be used to select a segment. For example, if surgical tool 112 has crossed an edge between two or more segments since the last time method 120 was executed, then one of the segments associated with the edge that was crossed may be selected. Alternatively, the segment being penetrated by surgical tool 112 may be selected. In step 128, the configuration of the selected segment is modified, preferably by extending the selected segment in a desired direction of movement of haptic device 113. The configuration flag may be set to indicate that haptic object 20 has been modified.

The method for modifying the configuration of the selected segment is preferably based at least in part on the manner in which the haptic object is represented. This representation may be based on surface polygons, voxels, non-uniform rational B-splines (NURBs), constructive solid geometry, and/or any other method for representing haptic objects now known or later developed. The modified segment may be represented in any manner which may or may not be the same as those used to represent the original haptic object. Preferably, the selected segment is extended such that the extended portion is continuous with the segment along one of its high curvature edges. The extension may be flat or curved. The segment may be extended a fixed or variable distance beyond the original segment, or could be extended to intersect another portion of the haptic object or the edge of a workspace. The method used for extending the segment depends on the method used for representing the extension. For example, if a haptic object is represented with surface polygons, then the polygons that lie within the segment of interest and adjacent to one of its boundaries are identified. A neighboring segment that lies beyond the original segment and has the same normal direction as the original polygon may be enabled. For a voxel representation, the voxels may be labeled to indicate whether they behave as solid or filled regions of space for configurations of the haptic object with different extended segments, which may be automatically, semi-automatically, or manually designed. The selected neighboring segment may be added to the haptic object. Thus, as illustrated in FIG. 6A, if portion 20' of haptic object 20 is the selected segment, then portion 20' may be extended beyond its original boundary, for example as shown by broken lines 23. Alternatively, if desired, a new haptic segment may be created in proximity to the selected segment.

In step 130, haptic interaction forces and/or torques for the haptic object are calculated. The haptic interaction forces and/or torques may be transformed and provided to haptic device 113. For example, it may be desirable to compute appropriate forces and torques for the actuators of the haptic device to apply such that the desired haptic interaction forces and/or torques will be produced. In some cases, it may be desirable to alter position or velocity commands to the actuators to produce the desired effect. The haptic interaction forces and/or torques from the selected segment may be used to guide haptic device 113 in a desired direction away from, toward, or aligned with physical object 114 to be sculpted. The haptic interaction forces and/or torques may be repulsive, attractive, frictional, viscous, impulsive, detent, regulatory (for example designed to maintain cutting speeds or feed rates), and/or the like. If desired, the haptic interaction forces and/or torques may be calculated using a mathematical, control theory, or machine learning algorithm.

If in step 124, it is determined that the criteria for modifying the configuration of haptic object 20 is not satisfied, then the process starting at step 130 may be executed.

If in step 122, it is determined that the configuration of haptic object 20 has already been modified, then in step 134, a determination is made as to whether one or more predefined criteria for maintaining haptic object 20 in the modified configuration is satisfied. These criteria may or may not be the same as those considered when the configuration of haptic object 20 was initially modified. Preferably, if at least one criterion for maintaining the haptic object in the modified configuration is satisfied, then the process starting at step 130 may be executed. Otherwise, in step 136, the modified haptic object is returned to its original configuration. The configuration flag may be reset to indicate that haptic object 20 has not been modified. After execution of step 136, the process starting at step 130 may be executed. In an alternative embodiment, the process starting at step 130 may be executed if in step 134 it is determined that a predefined logical combination of a set of criteria are satisfied.

As illustrated in FIG. 6A, when haptic device 113 or surgical tool 112 coupled to haptic device 113 comes within a predefined distance Ri of one portion of haptic object 20, say portion 20', that portion of haptic object 20 may be activated and modified such that it extends beyond its original boundary as shown by dashed lines 23. While haptic device 113 or surgical tool 112 is in close proximity to portion 20' or maintains contact with portion 20', portion 20' remains modified. Surgical tool 112 may be used during that time to sculpt the portion of physical object 114 corresponding to portion 20' to a desired shape. When the sculpting of the portion of physical object 114 corresponding to portion 20' is completed, the user may move haptic device 113 away from portion 20'. Portion 20' may then be returned to its original configuration. When haptic device 113 or surgical tool 112 moves to within a predefined distance of another portion of haptic object 20, say portion 20", portion 20" of haptic object 20 may be activated and modified such that it extends beyond its original boundary.

The illustrated method for dynamically modifying a haptic object may be used in a variety of applications, such as any procedure where a virtual constraint and/or haptic cues are used to guide a user using a haptic device for sculpting a physical object or shape that has high curvature. For example, the method may be used in fabrication of components for consumer or industrial products, for the reproduction or creation of artistic pieces, such as sculptures, for shaping bones in an orthopedic procedure, and/or the like.

The illustrated method for dynamically modifying a haptic object may be implemented in software, hardware, or a combination of both software and hardware. The steps discussed herein need not be performed in the stated order. Several of the steps could be performed concurrently with each other. Furthermore, if desired, one or more of the above described steps may be optional or may be combined without departing from the scope of the present invention.

A technical advantage of this exemplary embodiment for dynamically modifying a haptic object is that the sculpting of the physical object may be performed in a more controlled manner. Thus, during a surgical procedure, unintentional damage to parts of the body may be avoided and the user can feel more comfortable using the system. Another technical advantage is that the user does not have to move its attention away from the working volume when switching from one segment to another segment of the haptic object. Yet another technical advantage is that shapes with high curvature may be operated on more easily than if only the entire haptic object were used.

Figure 8:
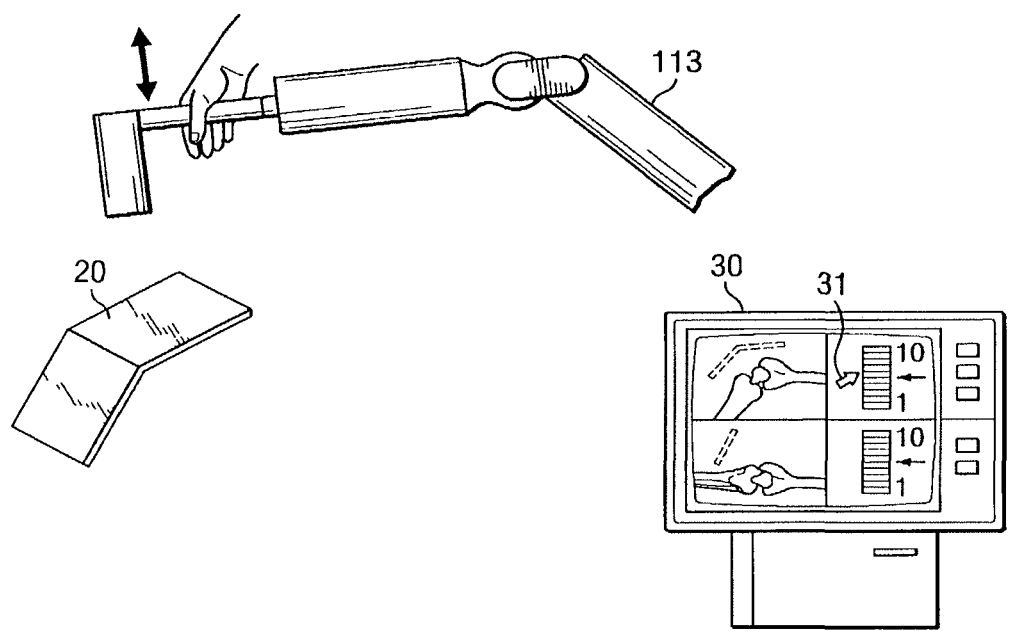
FIG. 8 illustrates the use of an exemplary haptic device as an input device.

FIG. 8 illustrates the use of an exemplary haptic device 113 as an input device. Haptic device 113 and a haptic object 20 in real space are illustrated. Haptic device 113 may also be used as an input device, allowing information to pass from the user to CAS system 11, and providing functionality similar to common user interface devices, such as a mouse, touchpad, keyboard, joystick, flight controller, haptic joystick, or any other input device. When used as an input device, it may be used for defining anatomical reference geometry, manipulating the position and/or orientation of virtual implants, manipulating the position and/or orientation of surgical approach trajectories, manipulating the position and/or orientation of bone resections, and the selection or placement of any other anatomical or surgical feature. Haptic device 113 may also be used for more generic user interface functions, including but not limited to, moving a cursor 31 (FIG. 8), selecting buttons or other similar user interface objects, selecting pull-down menus, manipulating on-screen dials, knobs, and other controls. When in this user-input mode the haptic device can be constrained to move in only certain directions which may be defined relative to the position of a predetermined portion of the haptic device, relative to the position of the patient or a portion of the patient anatomy, or relative to images or 3-D models of schematic, virtual, atlas, or actual patient anatomical features. The predetermined portion of the haptic device may be capable of moving.

As illustrated in display 30 of FIG. 8, haptic device 113 may be used as an input device to change the position, shape, size, etc. of haptic object 20. An example of an application of haptic device 113 used in this mode is planning the placement of a knee implant. After acquiring appropriate anatomical images of the anatomy of interest, the computer surgery system enters a mode where a cursor appears on a display visible to the user. The user grasps the arm to move the position of the cursor, possibly in multiple views. When satisfied with the position of the cursor, the user fixes it in the desired position through the use of a foot pedal, button, wired or wireless control pendant, voice command, or other input, or through the application of a force or torque to the haptic arm, or moving the haptic arm in a distinctive gesture, such as a tap, twist, or other gesture that is easily distinguishable from the user interactions during the cursor positioning. After the first position is set, a second cursor is used to define the endpoint of a line connecting to the two or three-dimensional position of the first cursor. The second cursor is moved, as above, to define an anatomical axis of the femur bone and its position is fixed using one of the above mentioned techniques. The two or three dimensional position and orientation of the implant can then be manipulated by the user using the haptic device as an input device. The implant is constrained by the system such that one of its surfaces is perpendicular to the anatomical reference line, but its position and orientation can be adjusted by the user. It is also possible to allow deviations from the anatomical axis, possibly coupled with displays of such deviations relative to anatomical reference frames familiar to the user. For example, the varus/valgus angle of the implant relative to the anatomical reference line can be adjusted and displayed to allow appropriate alignment of the knee implants. This general technique can be adapted to plan the approach and/or placement of minimally invasive hip and knee implants, trauma fixation pins, pedicle screws, biopsy needles, radioactive beads, radiotherapy beam emitter, or any other medical device.

With a haptic device, the surgeon can use tools identical or very similar to those used in standard practice. By exploiting the haptic features of the device, the need for awkward teach pendants or GUI-based robot controls may be reduced or eliminated. Switching between freehand and assisted steps of a procedure is quickly performed by simply pushing the device out of the way, similar to familiar operating room objects such as microscopes and overhead lights. While the systems may be internally complex, the surgeon must be shielded from this complexity so that he can focus all of his attention on his patient.

For example, the haptic arm can hold itself at a reference position using a joint-based or Cartesian control algorithm. The user applies forces and/or torques to the arm, either on an interaction handle or end-effector or at any point on the arm, which cause the arm to deflect from the reference position. The amount and direction of the deflection is continuously communicated to the computer system to modify the position of any desired virtual reference geometric feature or user interface object.

In another example, the haptic arm can hold itself at a reference position using a joint-based or Cartesian control algorithm but with two degrees of freedom left unconstrained. The user can then move the arm in the unconstrained directions to provide two-dimensional control of a user-interface object, such as a cursor, implant, or other geometric or virtual surface entity. A similar technique can be used for one degree of freedom manipulation of objects, such as user interface slider bars, implant lengths, positions of objects along a reference trajectory, or any other one-dimensional control such as audio volume, image brightness, object scaling, image zooming, and the like. A similar technique can be used for higher than three degree of freedom positioning of implants or virtual or haptic objects. The haptic object's position may also be constrained relative to any relevant anatomical features for a particular application. For example, a knee implant may be constrained to have the proper alignment relative to the anatomical axis of the leg, or to achieve proper ligament balance, but with the other degrees of freedom controllable by the user in the manner described above.

The stiffness or damping of the control algorithm may vary in different directions to indicate preferential directions of motion which may be aligned with any direction as described in the previous paragraph. This stiffness variation may include zero stiffness along certain directions or may lock the user to the preferred directions once the deviation from the reference position exceeds some threshold value. This stiffness variation assists with simplifying the planning process by allowing the user to focus their attention on a limited number of degrees of freedom at a time. For example, the user may set the position of an implant along one or two directions first, then set the position of the implant along an additional direction or directions without disturbing the set directions.

The stiffness and damping variations can occur automatically depending on the physical interaction of the user with the haptic device and does not require the use of another input device such as a voice command, control pendant, or foot pedal. Any such simplification has benefits in reducing service costs, simplified system use, and improved safety. This general method of planning also allows the surgeon to perform planning without having to leave the normal operating position to interact with the computer-aided surgery system or requiring an assistant to control the computer-aided surgery system or requiring the introduction of additional input devices other than the haptic device which is already being used for execution of the surgical plan. An additional benefit of this use of a haptic device is that the motion of the controlled object can be scaled relative to the motion of the arm, so that it can be positioned to a precision better than the user can position a real object, eliminating the deleterious effects of the user's hand tremor and any force disturbances arising from friction, backlash, magnetic detent forces, and other force disturbances arising from the haptic arm. It should be noted that the primary function of the object controlled by the haptic device is something other than monitoring the pose of the haptic device or monitoring the pose of a component of interest that may or may not be coupled to the haptic device.

Figure 7A:
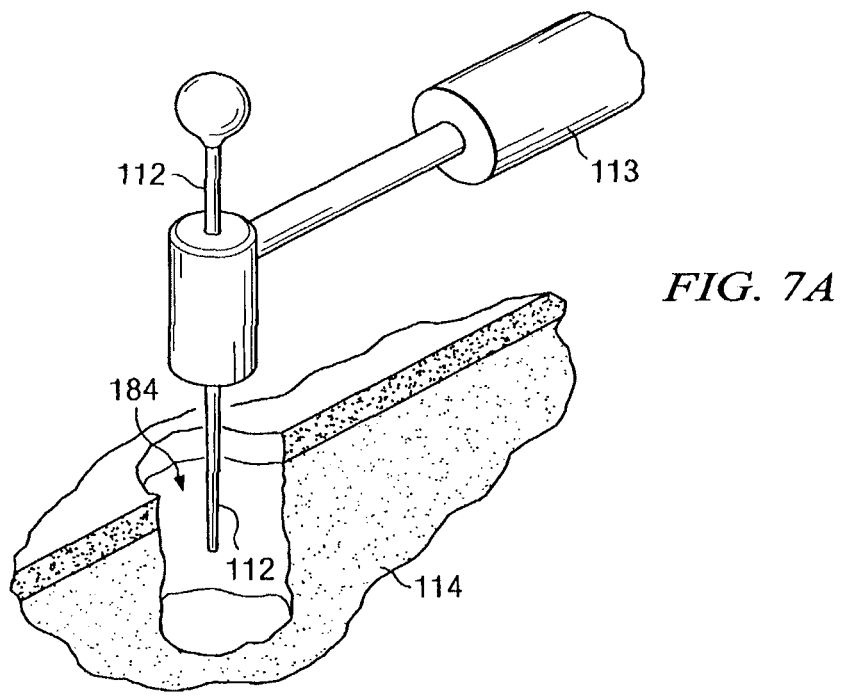
FIGS. 7A and 7B illustrate the use of an exemplary haptic device and a surgical tool to define a haptic object.
Figure 7B:
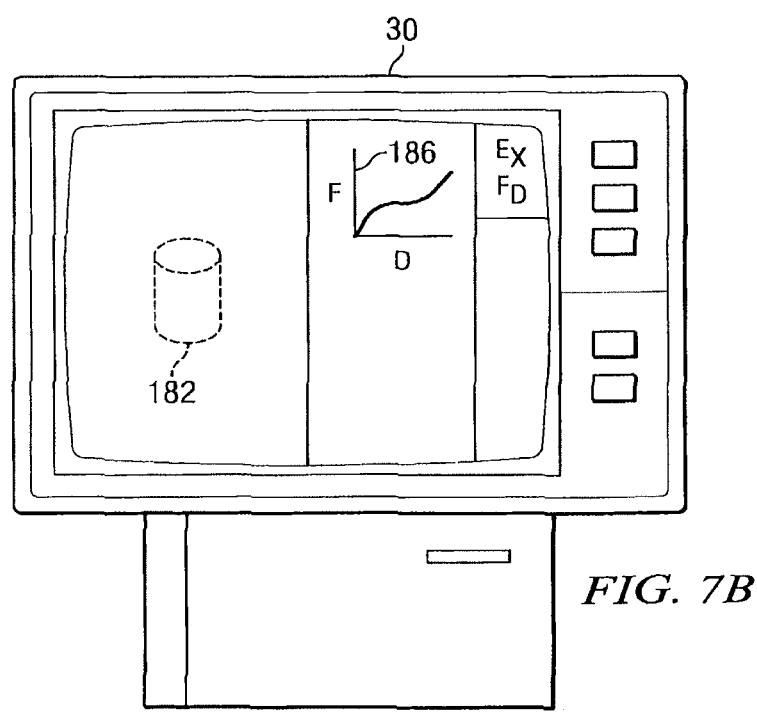

FIGS. 7A and 7B illustrate the use of a haptic device and a surgical tool to define a haptic object. In the illustrated example, haptic device 113 is being used as an input device to define haptic object 182. In order to use haptic device 113 as an input device to define haptic object 182, the user grasps surgical tool 112 coupled to haptic device 113. If desired, the user may grasp haptic device 113 itself. Using surgical tool 112 the user traces the boundaries of a desired region, for example a portion of the anatomy with respect to which the haptic object is to be defined. The user may trace the boundary, for example by touching the end of surgical tool 112 to portions of the desired region of the anatomy. The motion of surgical tool 112 may be recorded and the locations of the endpoints traced by the user computed. The geometry and/or location of haptic object 182 may be determined based at least in part on the location of the endpoints. A haptic device creation mode may be used to specify the desired shape of the haptic object. For example, to create a cylindrical haptic object that corresponds to a resected portion 184 of anatomy 114, the user can trace a plurality of points on the boundary of resected portion 184. An appropriate cylindrical haptic object may be created using any technique now known or later developed.

Material and other properties of the anatomy may be defined by probing the anatomy. For example, surgical tool 112 may include a force measurement device coupled to the tip of surgical tool 112. Alternatively, if desired, instead of surgical tool 112, a probe comprising a force measurement device may be coupled to haptic device 113. When the user interfaces the force measurement device against a portion of anatomy 114, the force may be measured by the force measurement device. The measured force may be displayed as a function of the distance the anatomy moves, if any, upon application of the force. The stiffness of that portion of anatomy 114 may be calculated as the ratio of the force to the distance. If desired, haptic device 113 itself may be interfaced with a portion of anatomy 114 and the force determined based on the torques provided by the actuators. In such an embodiment, haptic device 113 may make small or large movements or press against portions of anatomy 114 in an autonomous mode without any physical assistance from the user. The force may be determined using any Jacobian method now known or later developed. The graphical representation 186 of FIG. 7B illustrates the force with which surgical tool 112 comes in contact with anatomy 114 as a function of displacement of anatomy 114.

If desired, other types of sensing devices may be coupled to haptic device 113 or surgical tool 112 to determine other properties of anatomy 114. These properties may be used to determine the type of tissue that is in proximity to haptic device 113. Thus, haptic device 113 may be used to differentiate between hard and soft bones, healthy and diseases tissues, different types of healthy tissues, boundaries of anatomical structures, etc. Based on information received from haptic device 113, the type of the tissue may be automatically determined by CAS system 11 and displayed on display device 30.

Figure 9:
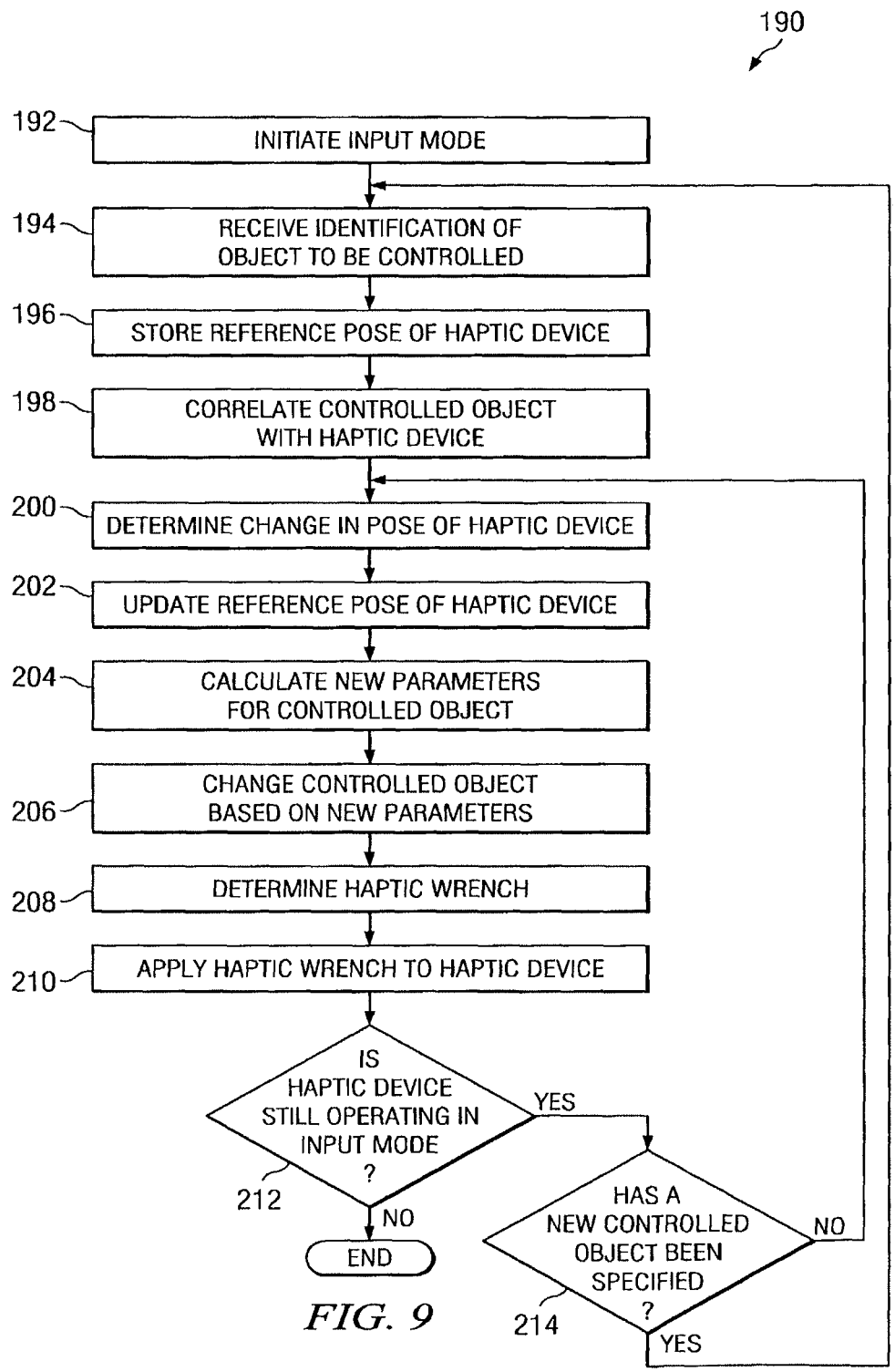
FIG. 9 is a flowchart of a representative method for using a haptic device as an input device.

FIG. 9 is a flowchart of a representative method 190 for using haptic device 113 as an input device. In step 192, the input mode is initiated. The user may initiate the input mode by any mechanism now known or later developed. For example, the user may use a graphical user interface, a footswitch, a keyboard, a button, and/or the like, to indicate that the user desires to use haptic device 113 as an input device. Haptic device 113 may control a plurality of objects. However, it is desirable that it only control a single object at one time. As such, in step 194, an identification of an object to be controlled is received. The controlled object may be a cursor, a button, an onscreen dial, a knob, a slider bar, or other similar user interface object, a virtual implant, a surgical approach trajectory, a bone resection, and/or the like. The user may select the object to be controlled by any method now known or later developed, for example by selecting the object using a conventional input device.

In step 196, a reference pose for haptic device 113 may be stored. The reference pose is preferably the current pose of haptic device 113. For example, in this step, position information about the tip of haptic device 113 may be stored. In step 198, the controlled object is correlated with haptic device 113. The correlation of the controlled object with haptic device 113 is desirable so that movement of haptic device 113 may be translated or mapped into a corresponding movement or action relative to the controlled object. The correlation or mapping allows a determination of the amount or direction of movement of the controlled object in response to movement of haptic device 113. For example, the user may specify that movement of haptic device 113 by one unit should cause a controlled object, for example cursor 31, to move by ten pixels on display device 30.

The user may move haptic device 113 around to control the object selected in step 194. In step 200, a change in pose of haptic device 113 is determined. The change in pose of haptic device 113 is preferably determined relative to the reference pose of haptic device 113. The change in pose of haptic device 113 may comprise, for example, a change in position of the tip of haptic device 113.

In step 202, the reference pose of haptic device 113 may be updated. Preferably, the reference pose is updated based at least in part on the change in pose of haptic device 113. If desired, the reference pose may be updated based at least in part on a wrench applied to haptic device by the user. The wrench may be explicitly measured by a sensor. If desired, the wrench may be implicit in that the haptic device can determine that a wrench is being applied.

In step 204, new parameters for the controlled object are calculated. The parameters of the controlled object may be, for example its pose, position, angle, size, color, shape, orientation, view direction, brightness, contrast, table indices, status, mode, configuration, and/or the like. The new parameters may be calculated based on the change in pose of haptic device 113 and/or the wrench applied to haptic device by the user. If desired, the new parameters may be calculated based on the change in reference pose of haptic device 113. Preferably, correlation information obtained in step 198 is used to calculate the new parameters. The new parameters may be used to change the controlled object. Thus, for example, when the controlled object is cursor 31 and there is a change in pose of haptic device 113, then a new pose for the controlled object may be determined based on the new parameters. In step 206, the controlled object is changed based on the new parameters. Thus, for example, if the controlled object is cursor 31, then the position of cursor 31 on display device 30 may be changed based at least in part on the new parameters calculated in step 204.

In step 208, a haptic wrench applied by the haptic device to the medical device and/or the user is determined. The haptic wrench may be determined based on the new parameters of the controlled object, the change in pose of haptic device 113, and/or the current pose of haptic device 113.

In step 210, the determined haptic wrench is applied to haptic device 113. Instead of allowing haptic device 113 to be moved in any direction, it may be desirable to constrain the movement of haptic device 113. The determined haptic wrench when applied to haptic device 113 prevents it from moving in certain undesirable directions. For example, if the controlled object is capable of moving in only one dimension, it may be desirable to constrain the motion of haptic device 113 so that haptic device 113 moves in only one direction. As another example, when the object being controlled is cursor 31 on display device 30, then it may be desirable to constrain the movement of haptic device 113 to a two-dimensional plane corresponding to display device 30. As a further example, if it is not desirable for haptic device 113 to move large distances from the reference pose, the haptic wrench may act to return haptic device 113 to the reference pose in one or more directions.

Within the input mode, haptic device 113 may be used in a position control mode or a rate control mode. In the position control mode, the change in pose of the controlled object tracks the change in pose of haptic device 113. For example, if haptic device 113 is moved in a particular direction by one unit, the controlled object moves in a corresponding direction by a corresponding amount. When haptic device 113 is released, it stays in its new pose.

On the other hand, in the rate control mode, the displacement of haptic device 113 from the reference pose and/or the wrench applied to the haptic device by the user, may control the velocity of the controlled object. For example, if haptic device 113 is maintained in its reference pose (or if no wrench is applied to the haptic device by the user), then the rate of movement of the controlled object is zero. The displacement of haptic device 113 from the reference pose (or the magnitude of the wrench applied by the user to the haptic device) determines the velocity of movement of the controlled object with the velocity of movement being proportional to the displacement of the controlled object (or to the magnitude of the wrench applied to the haptic device). When it is desirable to move the controlled object, haptic device 113 is simply moved (or pushed) in the direction of the desired motion of the controlled object. When haptic device 113 is released it moves back to the reference pose due to application, in step 210, of the haptic wrench determined in step 208. Thus, in the rate control mode, the controlled object may be moved a substantial distance without substantially moving haptic device 113.

In step 212, a determination is made as to whether haptic device 113 is still operating in the input mode. If haptic device 113 is not operating in the input mode, then the process terminates. Otherwise, in step 214, a determination is made as to whether a new object to be controlled has been specified. If a new object to be controlled has not been specified then the process starting at step 200 to determine the change in pose of haptic device 113 may be executed. Otherwise, the process starting at step 194 to receive identification of the new object to be controlled is executed.

For example, in one embodiment, the reference pose may be associated with the desired trajectory of a drill guide attached to haptic device 113. In such an embodiment, updating the reference pose in step 202 comprises changing the desired trajectory of the drill guide. When the user moves haptic device 113 from the reference pose for a prolonged period of time, the reference pose will be updated to move in the direction of the user's deflection. If, in step 210, an appropriate haptic feedback wrench is applied, then upon release of haptic device 113 by the user, haptic device 113 will assume the new reference pose. When the user is satisfied with the reference pose and the input mode is terminated in step 212, haptic device 113 will be in a pose such that the drill guide is aligned with the desired trajectory.

The illustrated method for using a haptic device as an input device may be implemented in software, hardware, or a combination of both software and hardware. The steps discussed herein need not be performed in the stated order. Several of the steps could be performed concurrently with each other. Furthermore, if desired, one or more of the above described steps may be optional or may be combined without departing from the scope of the present invention.

A technical advantage of using a haptic device as an input device in the manner described above is that the use of an additional input device may be avoided thereby reducing the clutter in the operating room.

What is claimed is:

1. A surgical system, comprising:
    a foot pedal;
    a touchscreen;
    a robotic arm;
    a constraint mechanism coupled to the robotic arm; and
    a computer system configured to:
        control the robotic arm to constrain manual movement of the constraint mechanism to a plane; and
        control the robotic arm to lock the constraint mechanism in a desired pose in response to the constraint mechanism moving to the desired pose via constrained manual movement in the plane and occurrence of both a user interacting with the foot pedal and the user providing input via the touchscreen.

2. The surgical system of claim 1, wherein the constraint mechanism is a drill guide.

3. The surgical system of claim 1, wherein controlling the robotic arm to lock the constraint mechanism in the desired pose comprises controlling hardware brakes of the robotic arm.

4. The surgical system of claim 1, wherein controlling the robotic arm to lock the constraint mechanism in the desired pose comprises controlling a servo of the robotic arm.

5. The surgical system of claim 1, wherein the computer system is further configured to control the robotic arm to counteract an effect of gravity on the constraint mechanism.

6. The surgical system of claim 1, wherein the plane is defined relative to an anatomical feature.

7. The surgical system of claim 6, further comprising a tracking system configured to provide tracking data indicative of a pose of the anatomical feature to the computer system.

8. The surgical system of claim 7, wherein the tracking system comprises a marker configured to be coupled to the anatomical feature and a camera configured to determine a location of the marker.

9. The surgical system of claim 8, wherein the computer system is configured to cause the touchscreen to display information superimposed over one or more images of the anatomical feature based on a position of the constraint mechanism.

10. The surgical system of claim 1, wherein the touchscreen is configured to display instructions for executing a surgical procedure using the surgical system.

11. The surgical system of claim 1, wherein the plane is defined based on x-ray images of a joint of a patient.

12. A computer-assisted surgery system, comprising:
a processor;
storage media coupled to the processor and storing instructions executable by the processor to cause the processor to perform operations comprising:
controlling a robotic arm to counteract an effect of gravity on a constraint mechanism coupled to the robotic arm while allowing manual movement of the constraint mechanism; and
controlling the robotic arm to constrain the manual movement to a plane; and
controlling the robotic arm to lock the constraint mechanism in a desired pose in response to the constraint mechanism moving to the desired pose and occurrence of both a user interacting with a foot pedal and the user providing input via a touchscreen.

13. The computer-assisted surgery system of claim 12, wherein the constraint mechanism is on the plane when in the desired pose.

14. The computer-assisted surgery system of claim 12, wherein the operations further comprise defining the plane relative to an anatomical feature of a patient.

15. The computer-assisted surgery system of claim 14, wherein defining the plane relative to the anatomical feature comprises receiving x-ray images of the anatomical feature of the patient.

16. The computer-assisted surgery system of claim 14, wherein the operations further comprise receiving tracking data indicative of a pose of the anatomical feature from a tracking system and determining a position of the plane based on the tracking data.

17. A method of operating a computer-assisted surgery system, comprising:
planning a bone resection to obtain a plane defined in relation to a position of an anatomical feature;
controlling mobility of a constraint mechanism mounted on a robotic arm by:
causing the robotic arm to limit manual movement of the constraint mechanism to the plane; and
manually manipulating the robotic arm to translate the constraint mechanism along the plane to a desired pose; and
causing the robotic arm to lock the constraint mechanism at the desired pose in response to the constraint mechanism moving to the desired pose via manual movement in the plane and the occurrence of a plurality of satisfaction indicators comprising two or more of a user interacting with a button, the user interacting with a foot pedal, the user interacting with a keyboard, the user interacting with a mouse, or the user providing input via a touch screen.

18. The method of claim 17, wherein the constraint mechanism is a drill guide.

19. The method of claim 18, further comprising causing the robotic arm to counteract effects of gravity on the constraint mechanism and the robotic arm.

20. The method of claim 19, wherein defining the plane in relation to the position of the anatomical feature comprises planning an alignment of a knee implant.

* * * * *